(12) United States Patent
Inghirami et al.

(10) Patent No.: US 7,732,592 B2
(45) Date of Patent: Jun. 8, 2010

(54) ALK PROTEIN TYROSINE KINASE, CELLS AND METHODS EMBODYING AND USING SAME

(75) Inventors: Giorgio Inghirami, Mt. Vernon, NY (US); Roberto Chiarie, Savigliano (IT)

(73) Assignee: New York University, New York, NY (US)

( * ) Notice: Subject to any disclaimer, the term of this patent is extended or adjusted under 35 U.S.C. 154(b) by 41 days.

(21) Appl. No.: 11/901,487

(22) Filed: Sep. 18, 2007

(65) Prior Publication Data
US 2008/0279870 A1    Nov. 13, 2008

Related U.S. Application Data

(62) Division of application No. 10/830,877, filed on Apr. 23, 2004, now Pat. No. 7,288,529.

(60) Provisional application No. 60/465,182, filed on Apr. 24, 2003.

(51) Int. Cl.
*C07H 21/04*    (2006.01)

(52) U.S. Cl. ................................... 536/24.5

(58) Field of Classification Search ................ None
See application file for complete search history.

(56) References Cited

U.S. PATENT DOCUMENTS

2001/0021505 A1    9/2001    Morris et al.

OTHER PUBLICATIONS

Piva et al. (2006) "Ablation of oncogenic ALK is a viable therapeutic approach for anaplastic large-cell lymphomas" Blood 107(2):689-697 showed inhibition of tumor cell growth in vitro and in vivo in a mouse using an shRNA comprising instant SEQ ID No. 5.*
Sausville et al. (2001) "Phase I Trial of 72-Hour Continuous Infusion UCN-01 in Patients With Refractory Neoplasms" J Clin Oncol 19:2319-2333.*
Brummelkamp et al. (2002) Science 296:550-552. cited by examiner.
Ritter et al. (2003) Oligonucleotides 13:365-373. cited by examiner.
Vickers et al. (2003) J. Biol. Chem. 278:7108-7118. cited by examiner.
Agrawal et al. Antisense therapeutics: is it as simple as complementary base recognition? 2000 Mol. Med. Today: Reviews. vol. 61, pp. 72-81.
Opalinska et al. Nucleic acid therapeutics: basic principlese and recent applications. 2002 Nature Reviews: Drug Discovery vol. 1, pp. 503-514.
Caplen RNAi as a gene therapy approach. Expt Opin. Biol. Ther. 2003, vol. 3, pp. 575-586.
Zhang, et al. Current Pharmaceutical Biotechnolongy 2004, vol. 5, p. 1-7.
Check, Nature, 2003, vol. 425, p. 10-12.
Elbashir et al. Duplexes of 21-nucleotide RNAs mediate RNA interference in cultured mammalian cells. 2001 Nature vol. 411:pp. 494-498.
Paddison et al. Stable suppression of gene expression by RNAi in mammalian cells 2002 Proc. Natl. Acad. Sci. vol. 99(3):pp. 1443-1448.
Johnston et al. Targeted inhibition of NPM-ALK gene expression with resultant decreased cell viability by tumor specific small interfering RNAs in anaplastic large cell lymphoma Nov. 2003 Blood vol. 102(11): 25A (Meeting Abstract #76).
Clare R. Ozawa, et al. Annl Rev of Pharm & Toxic., 40, 295-315 (2000).
U. Ritter, et al., Olligonucleotides, 13, 365-373 (2003).
Francesco Turturro, et al., Clinical Cancer Research, 8, 240-245 (2002).
Roberto Chiarle, et al., Blood, 101, 1919-1927 (2003).
Lorena Passoni, et al., Leukemia & Lymphoma, 44, 1675-1681 (2003).

* cited by examiner

*Primary Examiner*—Louis Wollenberger
(74) *Attorney, Agent, or Firm*—Klauber & Jackson, LLC

(57) ABSTRACT

The present invention provides for a transgenic animal model that constitutively expresses a protein encoded by the NPM-ALK gene in lymphoid tissue, and exhibits enhanced and accelerated development of a T cell lymphoproliferative disorder or B cell plasma cell tumor, together with the identification of cells transduced with the ALK tyrosine kinase gene or fusion proteins thereof, and methods for using this animal model and cells for screening compounds or treatments for antitumor activity. In preferred embodiments, the animal is a transgenic mouse that expresses a human NPM-ALK gene operably linked to human regulatory sequences, and the cells of the mouse have at least one copy of the NPM-ALK transgene, whereby the mouse constitutively expresses a protein encoded by the NPM-ALK transgene. The animals and cells of the invention are useful in the study of NPM-ALK-dependent lymphomagenesis and plasma cell tumors and in the development of treatments for these conditions.

3 Claims, 14 Drawing Sheets

ALK PROTEIN TYROSINE KINASE, CELLS AND METHODS EMBODYING AND USING SAME

CROSS-REFERENCE TO RELATED APPLICATIONS

The present application is a division of U.S. Ser. No. 10/830,877 filed Apr. 23, 2004, now U.S. Pat. No. 7,288,529 which is a non-provisional application claiming the priority of provisional U.S. Ser. No. 60/465,182, filed on Apr. 24, 2003, the disclosure of which is incorporated by reference herein in its entirety. Applicants claim the benefits of this application under 35 U.S.C §119(e).

GOVERNMENT RIGHTS CLAUSE

The research leading to the present invention was supported, at least in part, by National Institutes of Health grant number RO1-CA64033. Accordingly, the Government may have certain rights in the invention.

FIELD OF THE INVENTION

This invention relates to ALK protein tyrosine kinase and to transgenic animals that constitutively express the protein encoded by the NPM-ALK gene and which exhibit enhanced and accelerated development of T cell lymphoproliferative disorders or B cell plasma cell tumors. More particularly, the invention relates to methods for using these animals or cells derived thereof, for screening compounds or treatments for antitumor activity, and for preparation of vaccines.

BACKGROUND OF THE INVENTION

Human Anaplastic Large Cell Lymphomas (ALCL) are a unique subset of lymphomas partly distinguished by their co-expression of the CD30 antigen (Stein, H. et al. (2000), Blood 96:3681-3695). Classical cytogenetic studies demonstrated that ALCLs carry unique translocations within the p23 region of chromosome 2, (Rimokh R., et al. carry unique translocations within the p23 region of chromosome 2, (Rimokh R., et al., (1989), Br J Haematol. 71:31-36. Kaneko Y., et al. (1989), Blood. 73:806-813 and Le Beau, M M et al. (1989) Leukemia. 3:866-870). In 1994, Morris et al. cloned the t(2; 5) translocation and discovered that a novel tyrosine kinase gene, the Anaplastic Lymphoma Kinase (ALK), was fused to the NPM/B23 gene (Morris, S W et al. (1994) Science. 263:1281-1284). NPM participates in nucleocytoplasmic trafficking (Wang D., et al. (1993) Cell Mol Biol Res. 39:33-42 and Szebeni A. et al. (1999) Protein Sci. 8:905-912) and has been recently shown to regulate the duplication of centrosomes (Okuda, M. et al. (2000) Cell 103:127-140). The ALK gene encodes a tyrosine kinase receptor whose physiological expression is largely limited to neuronal cells (Iwahara, T. et al. (1997) Oncogene. 14:439-449 and Morris, S W, et al. (1997) Oncogene 14:2175-2188). However, the physiological role of the ALK receptor remains largely unknown since ALK$^{-/-}$ mice appear normal (Duyster, J. et al. (2001) Oncogene. 20:5623-5637). Nonetheless, ALK is phylogenetically highly conserved (Iwahara, T. et al. (1997) Oncogene. 14:439-449 and Morris, S W, et al. (1997) Oncogene. 14:2175-2188), suggesting that it might have an important role in neuronal cellular function. In fact when constitutively activated in the rat pheochromocytoma cells PC12, ALK leads to neuronal differentiation and provides anti-apoptotic signals in stress conditions (Souttou, B. et al. (2001) J Biol Chem. 276:9526-9531). (Piva et al. personal communication). Recently, Stoica et al. have also demonstrated that pheotrophin binds to ALK receptor (Stoica, G E, et al. (2001) J Biol Chem. 276:16772-16779), but other additional ligands might exist.

In the past five years, several groups have successfully cloned new ALCL translocations and demonstrated that the ALK gene can fuse to multiple targets, which include the TFG, TPM3, ATIC, CLTCL, RanBP2 and MSN genes (Duyster, J. et al. (2001) Oncogene. 20:5623-5637). Proteins fused to ALK largely determine the subcellular localization of the derived fusion proteins, being cytoplasmic (ATIC-, TGF-ALK etc.), cytoplasmic and nuclear (NPM-ALK), or membranous (MSN-ALK) (Duyster, J. et al. (2001) Oncogene. 20:5623-5637). Moreover, ALK translocations can also be detected in non-lymphoid neoplasms such as inflammatory myofibroblastic tumors (Coffin, C M. et al. (2001) Mod Pathol. 14:569-576), and ALK expression has been described in neuroblastomas (Lamant, L. et al. (2000) Am J Pathol. 156:1711-1721), as well as in a unique subtype of IgA positive plasmacytoid tumors (Delsol, G. et al. (1997) Blood. 89:1483-1490).

Cellular transformation by NPM-ALK has been demonstrated in immortalized rodent fibroblasts (Bai, R Y. et al. (1998) Mol Cell Biol. 18:6951-6961), and confirmed in studies which have shown that ALK protects Ba/F3 and PC12 cells from interleukin-3 or growth factor withdrawal (Stoica, G E., et al. (2001) J Biol Chem. 276:16772-16779 and (Bai R Y., et al. (1998) Mol Cell Biol. 18:6951-6961). (Piva et al. personal communication). Transfer of NPM-ALK transduced bone-marrow cells into irradiated host recipient mice resulted in the generation in vivo of large cell B cell lymphomas (Kuefer, M U. et al. (1997) Blood. 90:2901-2910). In the past few years, the molecular mechanisms of NPM-ALK-mediated cellular transformation have also been partially elucidated (Duyster, J. et al. (2001) Oncogene. 20:5623-5637). It has been shown that the ALK portion of the fusion protein, corresponding to the cytoplasmic tail of the ALK receptor and containing the catalytic domain, is absolutely required for transformation (Bai, R Y. et al. (1998) Mol Cell Biol. 18:6951-6961), whereas all the N-terminal regions of the ALK chimeras function as dimerization domains (Bischof, D. et al. (1997) Mol Cell Biol. 17:2312-2325) and (Duyster, J. et al. (2001) Oncogene. 20:5623-5637). As a result of spontaneous dimerization, ALK undergoes autophosphorylation and becomes catalytically active. Constitutively active ALK fusion proteins can bind multiple adaptor proteins and activate a series of pathways involved in cell proliferation, transformation and survival. These include the PLC-Shc PI3-K/Akt and the Jak3-Stat3 pathways (Bai, R Y. et al. (1998) Mol Cell Biol. 18:6951-6961; Bai R Y., et al. (2000) Blood. 96:4319-4327 and Zamo, A. et al. (2002) Oncogene. 21:1038-1047). All these molecules and their putative roles were identified using either non-hematopoietic cells or immortalized B cells, leaving the molecular mechanisms of T cell transformation by ALK chimeras still unknown.

Transgenic animals are among the most useful research tools in the biological sciences. These animals have a heterologous (i.e., foreign) gene, or gene fragment, incorporated into their genome that is passed on to their offspring. Although there are several methods of producing transgenic animals, the most widely used is microinjection of DNA into single cell embryos. These embryos are then transferred into pseudopregnant recipient foster mothers. The offspring are then screened for the presence of the new gene, or gene fragment. Potential applications for transgenic animals include discovering the genetic basis of human and animal diseases, generating disease resistance in humans and animals, gene therapy, drug testing, and production of improved agricultural livestock.

SUMMARY OF THE INVENTION

The present invention relates to the role of ALK tyrosine kinase in development of T cell lymphoproliferative disorders and B cell plasma cell tumors. More particularly, the invention relates to the production of a transgenic animal model and cell lines useful for identifying and assessing efficacy of new therapeutic regimens for the treatment of such tumors. In addition, the invention relates to the identification of nucleic acid sequences, in particular, small interfering RNA molecules capable of preventing expression of the ALK tyrosine kinase. The present invention demonstrates that constitutive activation of ALK chimeras results in cell transformation in vitro and leads to lymphoid neoplasms in transgenic animals, in vivo. A retroviral small interfering RNA (siRNA) vector against a common sequence of the catalytic domain of ALK was developed to stably abrogate the expression of all ALK oncogenic chimeras. Specific down-regulation of ALK protein expression in vitro was demonstrated. This subsequently leads to the down-regulation of downstream targets of ALK, such as STAT3 and JunB. ALK siRNA impairs the growth of ALK-inducible MEF in vivo and in vitro reverting their transformed phenotype. In addition the transduction of human lymphoma cell lines with ALK siRNA retroviral or lentiviral constructs results in growth impairment and cell death of ALK+ ALCL cells. Accordingly, targeting of ALK chimeras via siRNA might provide a new and effective approach in the treatment of ALK positive neoplasms.

It is thus an object of the invention to provide a transgenic animal model to aid in understanding the role of ALK in T cell transformation or in B cell plasma cell tumor formation, and to use this transgenic animal for identification of novel therapeutics for treatment of cancers associated with expression of ALK tyrosine kinase. In a specific embodiment, a transgenic animal model is provided which constitutively expresses NPM-ALK tyrosine kinase protein encoded by the NPM-ALK gene in lymphoid tissue, and exhibits enhanced and accelerated development of a T cell lymphoproliferative disorder or B cell plasma cell tumor. In a preferred embodiment, the transgenic animal is a mouse.

Accordingly, in a first aspect of the invention, NPM-ALK transgenic (Tg) mice are generated by injecting blastocysts with a construct in which the full-length cDNA of NPM-ALK chimera was placed under the control of the murine CD4 promoter. More particularly, the transgenic cassette (CD4 cassette) includes the minimal CD4 enhancer (339 base pair), the minimal murine CD4 promoter (487 base pair), the transcription initiation site, and 70 base pairs of the untranslated first exon and part of the first intron of the murine CD4 gene but lacks the CD8 silencer. Furthermore, the transgenic CD4 cassette allows for expression of the NPM-ALK gene in a number of subsets of T cells including CD4+/CD8+ early progenitor thymocytes, CD4+/CD8- T cells and CD4-/CD8+ T cells. All NPM-ALK Tg mice developed clonal lymphoproliferative disorders after a short period of latency. In addition to T cell lymphomas, a sizable fraction of these mice also acquired B cell plasma cell neoplasms. Studies utilizing these NPM-ALK Tg mice will allow a better understanding of the molecular mechanisms and genetic defects leading to ALK-mediated transformation.

A second aspect of the invention provides for a transgenic animal whose genome comprises a transgene encoding NPM-ALK operably linked to a CD4 promoter, wherein the animal is heterozygous for the transgene. Furthermore, the NPM-ALK fusion gene encodes a fusion protein capable of binding mouse Shc, IRS-1, Grb-2, PI3K, Stat and Jak proteins.

A third aspect of the invention provides for a transgenic animal which exhibits constitutive phosphorylation of Stat3 and Jak3 in cells.

A fourth aspect of the invention provides for a transgenic animal whose genome comprises a human NPM-ALK gene operably linked to human regulatory sequences, the animal comprising at least one NPM-ALK allele, wherein the animal constitutively expresses the NPM-ALK gene, exhibits increased expression of the tyrosine kinase protein, and further exhibits accelerated development of a T cell lymphoproliferative disorder or B cell plasma cell tumor.

A fifth aspect of the invention provides for an isolated animal cell comprising a transgene, wherein the transgene comprises a DNA sequence encoding NPM-ALK operably linked to a CD4 promoter, and wherein the cell is isolated from tissue containing T lymphocytes or thymocytes. In a preferred embodiment, the cell is isolated from a T cell lymphoma.

A sixth aspect of the invention provides for an isolated animal cell comprising a transgene, wherein the transgene comprises a DNA sequence encoding NPM-ALK operably linked to a CD4 promoter, and wherein the cell is isolated from tissue containing B lymphocytes. In a preferred embodiment, the cell being isolated is from a plasma cell tumor.

A seventh aspect of the invention provides for a method for screening a compound for antitumor activity, comprising administering to a transgenic animal the compound, in which the transgenic animal constitutively expresses a protein encoded by the NPM-ALK gene in at least one tissue, wherein the transgenic animal exhibits accelerated development of a T cell lymphoproliferative disorder or a B cell plasma cell tumor; and monitoring the antitumor activity of the compound.

An eighth aspect of the invention provides for a method for screening a cancer treatment for antitumor efficacy and/or activity, comprising administering to an animal bearing a tumor the cancer treatment and monitoring the antitumor activity of the cancer treatment. In a particular embodiment, the animal is a transgenic animal which constitutively expresses a protein encoded by the NPM-ALK gene in lymphoid tissue, and wherein the transgenic animal exhibits accelerated development of a T cell lymphoproliferative disorder or a B cell plasma cell tumor. In another embodiment, the animal is a nude mouse, wherein said mouse bears a tumor that expresses the ALK tyrosine kinase gene and the effectiveness of cancer therapy is assessed by measuring the growth of said tumor over time.

A ninth aspect of the invention provides for a method for screening a compound for antitumor activity, comprising contacting a tumor cell with the test compound, wherein the tumor cell expresses a protein encoded by the NPM-ALK gene, and monitoring the antitumor activity of the test compound. In one particular embodiment, the cell is obtained from a transgenic animal which expresses the NPM-ALK gene in lymphoid tissue, and wherein the transgenic animal exhibits accelerated development of a T cell lymphoproliferative disorder or a B cell plasma cell tumor.

In another particular embodiment, the method of screening a test compound for anti-tumor activity comprises:
 (a) transfecting a cell line with the NPM-ALK gene which is operably linked to a tetracycline responsive element;
 (b) exposing the cells to a tetracycline, resulting in cellular changes and cell death;

(c) treating a portion of the cells with a test compound either prior to, concurrently, or subsequent to, tetracycline induction of the NPM-ALK gene; and (d) monitoring cellular changes and cell death in the cultures exposed to the test compound and comparing the cellular changes and cell death in a sample of cells not treated with test compound. In a particular embodiment, the cells may be selected from the group consisting of h293T, GP-293, and MEF Tet-Off cells. In yet another particular embodiment, the tetracycline is doxycyclin.

A tenth aspect of the invention provides for a method of treating cancers by administering a compound identified by the screening methods described herein. In a particular embodiment, the compounds identified by the screening methods of the present invention inhibit expression and/or activity of ALK tyrosine kinase. In another particular embodiment, the inhibitors of ALK tyrosine kinase are selected from the group consisting of proteins or peptides, nucleic acid molecules, small synthetic organic compounds, and antibodies or fragments thereof that inhibit the expression and/or function of ALK tyrosine kinase. In yet another particular embodiment, the nucleic acid molecules that inhibit the expression and/or function of ALK tyrosine kinase are antisense nucleic acids or small interfering RNA molecules. In yet another particular embodiment, the ALK tyrosine kinase inhibitor is a small interfering RNA molecule comprising the nucleic acid sequence of any of SEQ ID NOs: 1-6. In a preferred embodiment, the small interfering RNA molecule comprises the nucleic acid sequence of SEQ ID NO: 5. In another embodiment, the cancers that are treatable by the compounds identified herein are cancers that are induced through activation of ALK tyrosine kinase. Non-limiting examples of such cancers include lymphoid tumors selected from the group consisting of anaplastic large cell lymphomas (ALCL), T cell lymphomas, B cell lymphomas and multiple myeloma.

An eleventh aspect of the invention provides for a vaccine specific for any tumor expressing an ALK tyrosine kinase, comprising an inhibitor of ALK tyrosine kinase coupled to a pharmaceutically acceptable carrier molecule. In a particular embodiment, administration of an antisense or small interfering RNA molecule is preferred.

A twelfth aspect of the invention provides an isolated siRNA molecule specific for the ALK tyrosine kinase gene, said siRNA molecule comprising the nucleic acid sequence of SEQ ID NOs: 1-6, wherein said siRNA molecule inhibits the proliferation of tumor cells. In a particular embodiment, the nucleic acid of SEQ ID NO: 5 (designated A5) is preferred.

A thirteenth aspect of the invention provides a method of inducing a tumor cell to undergo apoptosis comprising administering an antagonist to ALK tyrosine kinase in the tumor cell, wherein said administering results in tumor cell death and/or prevention from metastasis. In a particular embodiment, the antagonist is selected from the group consisting of protein or peptide, a nucleic acid molecule, an antibody, a small synthetic organic compound, an antisense nucleic acid molecule and a small interfering RNA molecule. In a yet further particular embodiment, the antagonist comprises the nucleic acid molecule of SEQ ID NOs: 1-6 and a pharmaceutically acceptable carrier. In a particular embodiment, the nucleic acid of SEQ ID NO: 5 is the preferred embodiment.

A fourteenth aspect of the invention provides for pharmaceutical compositions comprising an inhibitor of the ALK tyrosine kinase and a pharmaceutically acceptable carrier. In one particular embodiment, the inhibitor is selected from the group consisting of a protein or peptide, a small synthetic organic molecule, a nucleic acid molecule, and an antibody or fragments thereof specific for ALK tyrosine kinase. In a yet further particular embodiment, the nucleic acid inhibitor is an isolated aritisense nucleic acid or a siRNA molecule and a pharmaceutically acceptable carrier, wherein said composition is effective in treating tumor cells that contain the ALK gene.

Other advantages of the present invention will become apparent from the ensuing detailed description taken in conjunction with the following illustrative drawings.

DETAILED DESCRIPTION

Figure 1:
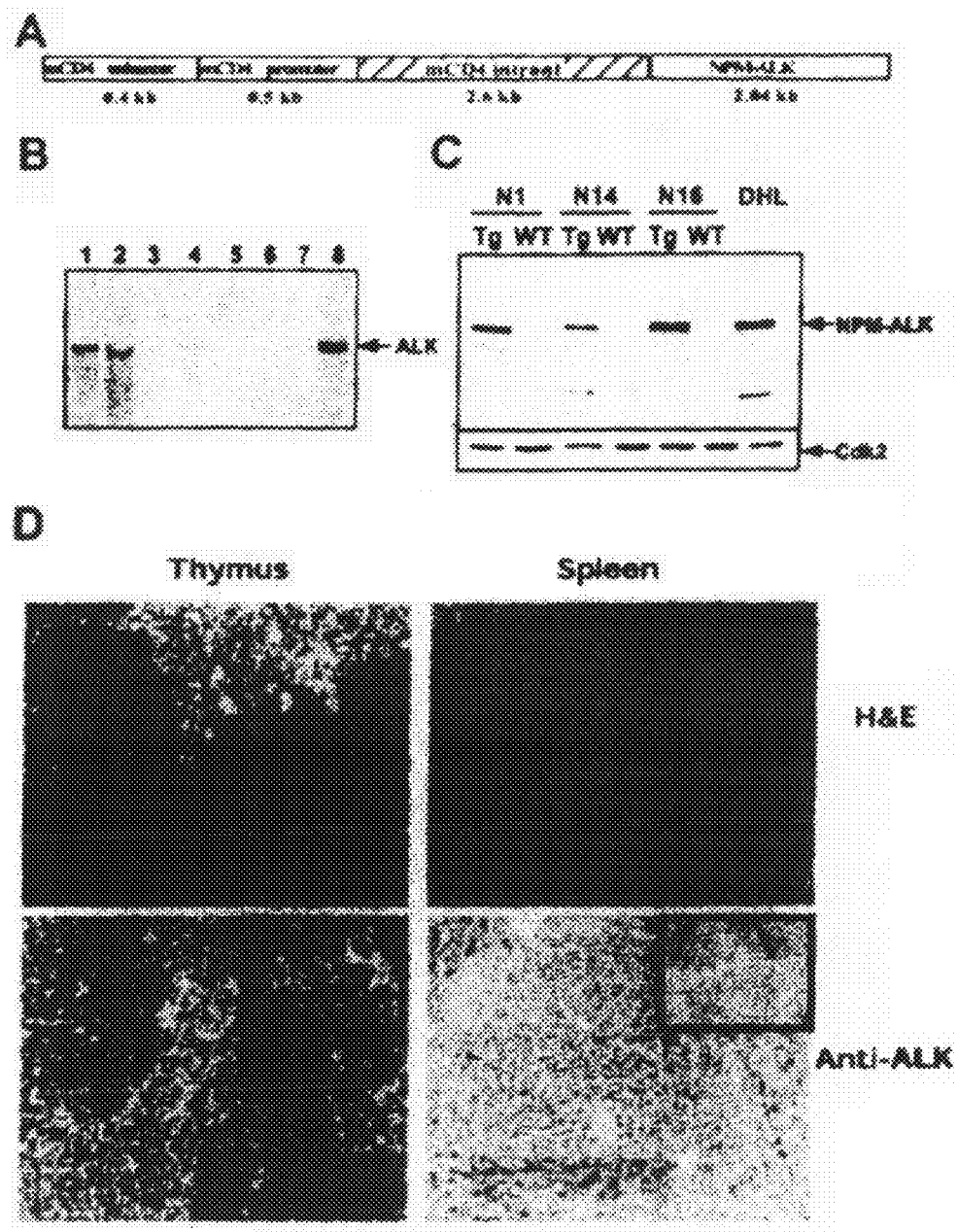
FIG. 1. Generation of NPM-ALK Tg mice. (A) NPM-ALK cDNA was cloned into a construct containing the CD4 enhancer and promoter as described herein (B) Southern blotting of representative animals obtained from different foster mothers. BamHI-digested DNAs were hybridized with a radio-labeled ALK cDNAprobe (1 N1, 2 N16, 4 N15, and 8 N8. Lane 3, 5, 6, and 7 correspond to correspondent normal littermate). (C) The expression and size of the fusion protein was characterized by Western blot. Proteins were extracted from thymi of Tg (N1, N14, and N16) and wild-type (WT) mice and loaded onto SDS-PAGE gel. The expression of the NPM-ALK chimera was detected with polyclonal rabbit anti-ALK antibody. The protein extract from the humanALCL-derived cell line DHL was used as a control. The loading was checked by Western blot for the ubiquitous CDK2 protein. (D) Histology of NPM-ALK Tg mice. Tg thymus (left panels) or spleen (right panels) were fixed in formalin and embedded in paraffin. Hematoxylin and eosin stains (top panels, 100×) showed normal thymus and spleen architecture in the preneoplastic tissue. Immunostaining with anti-ALK antibody (bottom panels) demonstrated a diffuse positivity in Tg thymocytes with stronger signal in medullary lymphocytes (100×). In Tg spleen the ALK positivity was localized in the periarteriolar T cell areas of the white pulp (400×). Left insert shows a nuclear and cytoplasmic staining in Tg lymphocytes (400×); right insert shows a lower magnification of the spleen (100×).

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entireties.

Definitions

As noted above, the terms used herein have the meanings recognized and known to those of skill in the art. However, for convenience and completeness, particular terms and their meanings are set forth below.

"Treatment" refers to the administration of medicine or the performance of medical procedures with respect to a patient, for either prophylaxis (prevention) or to cure the infirmity or malady in the instance where the patient is afflicted.

The term "antibody" as used herein includes intact molecules as well as fragments thereof, such as Fab and F(ab')$_2$, which are capable of binding the epitopic determinant. Antibodies that bind NPM-ALK gene product can be prepared using intact polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g, a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397.). The antibody may be a single chain antibody. The antibody may be a human or a humanized antibody. The antibody may be prepared in mice, rats, goats, sheep, swine, dogs, cats, or horses. A "blocking antibody" refers to an antibody that interferes with the function, activity or expression of a particular molecule, in the matter of the present invention, an antibody to ALK tyrosine kinase.

"Apoptosis" refers to "programmed cell death" and is characterized by certain cellular characteristics such as condensation of the chromatin and by DNA fragmentation and a positive "TUNEL" staining pattern.

"Subject" or "patient" refers to a mammal, preferably a human, in need of treatment for a condition, disorder or disease.

A "therapeutically effective amount" is an amount sufficient to decrease or prevent the symptoms associated with a T cell lymphoproliferative disorder or B cell plasma cell tumor or an amount sufficient to result in inhibition of growth of the cancer cells or a decrease in proliferation of cancer cells resulting from the presence of the NPM-ALK gene.

By "operably linked" is meant that a gene and a regulatory sequence are connected in such a way as to permit expression of the gene product under the control of the regulatory sequence.

By "transgenic" is meant any animal which includes a nucleic acid sequence which is inserted by artifice into a cell and becomes a part of the genome of the animal that develops from that cell. Such a transgene may be partly or entirely heterologous to the transgenic animal. Although transgenic mice represent a preferred embodiment of the invention, other transgenic mammals including, without limitation, transgenic rodents (for example, hamsters, guinea pigs, rabbits, and rats), and transgenic pigs, cattle, sheep, and goats are included in the definition.

As used herein a "small organic molecule" is an organic compound (or organic compound complexed with an inorganic compound (e.g., metal)) that has a molecular weight of less than 3 kilodaltons, and preferably less than 1.5 kilodaltons.

A "vector" is a replicon, such as plasmid, phage, virus, or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein the terms "fusion protein" and "fusion peptide" are used interchangeably and encompass "chimeric proteins and/or chimeric peptides" and fusion "intein proteins/peptides". A fusion protein of the present invention can comprise at least a portion of a protein of the present invention, for example, joined via a peptide bond to at least a portion of another protein or peptide including a second protein in a chimeric fusion protein.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut-oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

RNA interference (RNAi) is an evolutionarily conserved mechanism in plant and animal cells that directs the degradation of messenger RNAs homologous to short double-stranded RNAs termed "small interfering RNA (siRNA)". The ability of siRNA to direct gene silencing in mammalian cells has raised the possibility that siRNA might be used to investigate gene function in a high throughput fashion or to modulate gene expression in human diseases. Methods of preparing siRNAs are known to those skilled in the art. The following references are incorporated herein by reference in their entirety: Reich et al., *Mol. Vis.* 9:210-6 (2003); Gonzalez-Alegre P et al., *Ann Neurol.* 53:781-7 (2003); Miller et al., *Proc Natl Acad Sci USA.* (2003); Bidere et al., *J Biol Chem.*, published as manuscript M301911200 (Jun. 2, 2003); Van De Wetering et al., EMBO Rep. 4:609-15 (2003); Miller and Grollman, *DNA Repair (Amst)* 2:759-63 (2003); Kawakami et al., *Nat Cell Biol.* 5:513-9 (2003); Abdelrahim et al., *Mol Pharmacol.* 63:1373-81 (2003); Williams et al., *J Immunol.* 170:5354-8 (2003); Daude et al., *J Cell Sci.* 116:2775-9 (2003); Jackson et al., *Nat. Biotechnol.* 21:635-7 (2003); Dillin, *Proc Natl Acad Sci U S A.* 100:6289-91 (2003); Matta et al., *Cancer Biol Ther.* 2:206-10 (2003); Wohlbold et al., Blood. (2003); Julien and Herr, *EMBO J.* 22:2360-9 (2003); Scherr et al., *Cell Cycle.* 2:251-7 (2003); Giri et al., *J. Immunol.* 170:5281-94 (2003); Liu and Erikson, *Proc Natl Acad Sci USA.* 100:5789-94 (2003); Chi et al., *Proc Natl Acad Sci USA.* 100:6343-6 (2003); Hall and Alexander, *J Virol.* 77:6066-9 (2003). In the matter of the present invention, the term "shRNA" refers to the short hairpin RNA that was generated as a small interfering RNA molecule with specificity for the ALK tyrosine kinase gene.

General Description

Anaplastic Large Cell Lymphomas (ALCLs) carry translocations in which the anaplastic lymphoma kinase (ALK) gene is juxtaposed to various genes, the most common of which is the NPM/B23 gene. ALK fusion proteins result in the constitutive activation of ALK tyrosine kinase, thereby enhancing proliferation and increasing cell survival. A direct role for NPM-ALK in cellular transformation has been shown in vitro with immortalized cell lines and in vivo using retroviral transfer experiments. Nonetheless, there is no direct evidence of its oncogenic potential in T lymphocytes, which represent the most common target of ALK chimeras.

Thus, it is an object of the present invention to provide a new transgenic animal model of lymphomagenesis in which human NPM-ALK transcription is targeted to T cells. Accordingly, NPM-ALK transgenic mice were generated by injecting blastocysts with a construct in which the full-length cDNA of NPM-ALK chimera was placed under the control of the murine CD4 promoter. More particularly, the transgenic cassette (CD4 cassette) included the minimal CD4 enhancer (339 base pair), the minimal murine CD4 promoter (487 base pair), the transcription initiation site, and 70 base pair of the untranslated first exon and part of the first intron of the murine CD4 gene but lacked the CD8 silencer. Furthermore, the transgenic CD4 cassette allows for expression of the NPM-ALK gene in a number of subsets of T cells including CD4+/CD8+ early progenitor thymocytes, CD4+/CD8– T cells and CD4–/CD8+ T cells. All NPM-ALK Tg mice developed clonal lymphoproliferative disorders after a short period of latency. In addition to T cell lymphomas, a sizable fraction of these mice also acquired B cell plasma cell neoplasms. Moreover, the invention provides for a transgenic mouse whose genome comprises a transgene encoding NPM-ALK operably linked to a CD4 promoter, wherein the transgenic mouse constitutively expresses NPM-ALK tyrosine kinase protein in lymphoid tissue, constitutively activates Jak3 and Stat3, encodes a fusion protein capable of binding Shc, IRS-1, Grb-2, PI3K, Stat and Jak proteins, and exhibits accelerated development of a T cell lymphoproliferative disorder or B cell plasma cell tumor. Thus, the present invention provides for a novel transgenic mouse which demonstrates the tumorigenic activity of ALK in vivo and also shows that ALK can efficiently transform T lymphocytes and can also lead to the development of B cell plasma cell tumors resembling multiple myeloma. Furthermore, the invention provides evidence that the ALK gene is not only capable of transforming cells, it is necessary to maintain the transformed phenotype. Accordingly, this particular transgenic mouse provides a means for testing new therapeutic regimens and for screening and identifying novel compounds for use in treating cancers, including but not limited to, ALCL, T and B cell lymphomas and multiple myelomas.

As shown herein, NPM-ALK transgenic (Tg) mice were born with the expected mendelian distribution, normal lymphoid organs, and a normal number and proportion of helper and suppressor T cells. However, after a short period of latency, all NPM-ALK Tg mice developed malignant lymphoproliferative disorders (mean survival, 18 weeks). NPM-ALK Tg thymic lymphomas displayed a T-cell phenotype characteristic of immature thymocytes and frequently coexpressed surface CD30. A subset of the NPM-ALK Tg mice also developed clonal B-cell plasma cell neoplasms. These tumors arose in peripheral lymphoid organs (plasmacytomas) or within the bone marrow and often led to peripheral neuropathies and limb paralysis. These NPM-ALK Tg mice are a suitable model to dissect the molecular mechanisms of ALK-mediated transformation, maintenance of the transformed phenotype and to investigate the efficacy of new therapeutic approaches for the treatment of human ALCL in vivo.

Methods for screening a compound for antitumor activity, or methods for screening a cancer treatment for antitumor activity, comprising administering to the transgenic animals of the present invention, the compound, or the cancer treatment, in which the transgenic animals constitutively express a protein encoded by the NPM-ALK gene in lymphoid tissue, is envisioned. Accordingly, wherein the untreated transgenic animals exhibit accelerated development of a T cell lymphoproliferative disorder or a B cell plasma cell tumor; animals receiving a test compound or test cancer treatment which is efficacious will demonstrate a decrease in tumor growth and may exhibit prolonged life spans. Thus, monitoring the antitumor activity of the test compound or the antitumor activity of the cancer treatment are envisioned by utilizing the transgenic animals and the methods of the present invention.

In addition, it is envisioned that tumors containing the ALK tyrosine kinase gene may be transplanted to other mouse strains, such as nude mice, which provide a means for studying human tumors containing the ALK tyrosine kinase gene and also provide a means of identifying and assessing potential new therapies.

Further aspects of the present invention provide for removal of cells from the transgenic animals and using these cells for screening of new anticancer compounds or treatment regimens.

Furthermore, other cells or cell lines may be transfected with the ALK tyrosine kinase gene and these cells may be used for screening new therapeutic agents for inhibition of cellular proliferation in vitro. In addition, the growth of these tumor cells can be assessed in vivo following transplant into animal models, such as nude mice. Novel therapeutic agents can then be tested in mice bearing these tumor cells containing the ALK tyrosine kinase gene or a fusion protein thereof.

A further aspect of the invention provides for an isolated animal cell comprising a transgene, wherein the transgene comprises a DNA sequence encoding NPM-ALK operably linked to a CD4 promoter, and wherein the cell is isolated from tissue containing T lymphocytes or thymocytes. A preferred embodiment provides for isolation of the animal cell from a T cell lymphoma.

A yet further aspect of the invention provides for an isolated animal cell comprising a transgene, wherein the transgene comprises a DNA sequence encoding NPM-ALK operably linked to a CD4 promoter, and wherein the cell is isolated from tissue containing B lymphocytes. A preferred embodiment provides for isolation of the animal cell from a plasma cell tumor. Such plasma cell tumors may be obtained from the lymphoid tissue or bone marrow of the transgenic animals, or they may be obtained from ascites fluid.

Thus, cells derived from tissues of the transgenic animals of the present invention, including, but not limited to T or B cells, and which harbor the NPM-ALK gene, may exhibit signs of cellular transformation and may demonstrate increased tumorigenic capacity. These cells, when incubated with test compounds that demonstrate anti-cancer potential, will exhibit diminished cellular changes associated with transformation and tumorigenicity, as compared to cells not treated with a compound that has anti-cancer potential. Methods for monitoring cellular changes and/or cell death are known to those skilled in the art.

Accordingly, a method for screening a test compound for antitumor activity, comprising contacting a cell isolated from the transgenic animals of the present invention with the compound, in which the transgenic animals constitutively express a protein encoded by the NPM-ALK gene in lymphoid tissue, wherein the transgenic animals exhibit accelerated development of a T cell lymphoproliferative disorder or a B cell plasma cell tumor; and monitoring the antitumor activity of the test compound on the cell by determination of cell viability, is envisioned by the present invention.

In a preferred embodiment, a method of screening a test compound for anti-tumor activity is envisioned, comprising:

(a) transfecting a cell line with the NPM-ALK gene which is operably linked to a tetracycline responsive element;

(b) exposing the cells to tetracycline, resulting in cellular changes and cell death;

(c) treating a portion of the cells with a test compound either prior to, concurrently, or subsequent to, tetracycline induction of the NPM-ALK gene; and (d) monitoring cellular changes and cell death in the cultures exposed to the test compound and comparing the cellular changes and cell death in a sample of cells not treated with test compound. In a particular embodiment, the cells are the h293T cell line and the tetracycline is doxycyclin.

A yet further aspect of the invention provides for methods of treating cancers, comprising administration of a compound identified by the methods described herein.

A preferred embodiment provides for administration of a compound that inhibits ALK. A non-limiting example of a cancer that may respond to the therapies envisioned by the methods of the present invention include cancers that are induced through activation of ALK tyrosine kinase. Such cancers may include, but are not limited to T or B cell cancers, such as anaplastic large cell lymphomas (ALCL), T or B cell lymphomas or multiple myeloma.

A further aspect of the invention provides for a vaccine comprising an inhibitor of the ALK tyrosine kinase coupled to a pharmaceutically acceptable carrier molecule. In a particular embodiment, the vaccine would comprise a nucleic acid molecule such as an antisense molecule or a small interfering RNA molecule having specificity for ALK tyrosine kinase. Thus, administration of such a vaccine may result in reduction of the tumor burden and increase in life-span of the immunized subjects.

Preparation of Transgenic Animals

Methods for preparing transgenic animals are well known to those of skill in the art. Accordingly, the invention provides for making a transgenic, non-human vertebrate animal containing heterologous DNA by any of the known methods. One non-limiting example may provide for first producing an embryonal cell of the non-human vertebrate animal with a targeted exon by first, generating a pool of bacteria containing plasmids into which have been randomly integrated a transposon including heterologous DNA; second, isolating from the pool a bacterium which contains a plasmid into which the transposon is integrated into a copy of the exon on the plasmid by assessing PCR amplification products generated from the pool using primers specific for the exon; third, introducing the plasmid of the bacteria into the embryonal cells under conditions that promote homologous recombination; and fourth, screening genomic DNA of the embryonal cells to identify an embryonal cell in which there has occurred integration of the heterologous DNA into the exon. The identified embryonal cell is then grown to generate the transgenic animal.

In one embodiment of this aspect of the invention, the animal expresses an enhanced level of the protein encoded by the gene of the exon. In another embodiment, the animal expresses a fusion protein product encoded by the gene of the exon and the heterologous DNA, or portion thereof. In another embodiment, the animal expresses a product, which may be a fusion protein, encoded by the heterologous DNA, or portion thereof. In yet another embodiment, the gene is placed under the control of the CD4 promoter.

In a preferred embodiment, NPM-ALK transgenic mice are generated by injecting Swiss-Webster blastocysts with a construct in which the full length cDNA of NPM-ALK chimera was placed under the control of the murine CD4 promoter. The transgenic cassette (CD4 cassette) included the minimal CD4 enhancer (339 bp), the minimal murine CD4 promoter (487 bp), the transcription initiation site, and 70 bp of the untranslated first exon and part of the first intron of the murine CD4 gene but lacked the CD8 silencer (Sawada, S. et al. (1994) Cell. 77:917-929). The NPM-ALK founders were back-crossed into Balb/c and C57B/6 strains and housed in a germ-free facility (Skirball Institute of Biomolecular Medicine, New York University School of Medicine). Positive NPM-ALK mice were detected by PCR using genomic DNA obtained from mouse tail biopsies as previously described (Chiarle, R. et al. (1999) J Immunol. 163:194-205). All experiments presented in this study were derived from mice (C57BU/6 and Balb/c backgrounds) obtained from two independent transgenic lines (N1 and N16). cul1 Tg mice were obtained placing (SacI/SalI) the human Cul1-N252 cDNA (encoding 1 to 252 (N252) amino terminal residues) into the CD4 cassette Tg (Piva, R. et al. Molecular and Cellular Biology In press). Screening of founder animals and their corresponding offspring was performed by PCR and confirmed by Southern hybridization on genomic DNA from tail biopsies. Rag2−/− mice were purchased from Taconic (Taconic, Germantown, N.Y.).

The present invention provides for a novel transgenic mouse model of NPM-ALK induced lymphomagenesis and demonstrates that human NPM-ALK leads to cell transformation and invariably to the generation of T cell lymphomas and plasma cell tumors. Furthermore, the results presented herein provide proof that the ALK gene is necessary for maintenance of the transformed state. The findings presented herein also demonstrate that ALK can efficiently bind a series of mouse adaptor proteins and result in the constitutive activation of Jak3 and Stat3.

Screening Assays

The invention provides for identification of agents (e.g., chemical compounds, carbohydrates, proteins, peptides, antibodies or nucleotides) that block the activity of the ALK tyrosine kinase. In one embodiment, a method of identifying such agent utilizes a cell line whose growth is inhibited upon activation of the NPM-ALK gene. Furthermore, the activation of the NPM-ALK gene ultimately results in death of the cell. Incubation of this cell line either before, during or after activation of the ALK gene with an agent that inhibits the activity of the ALK gene would be identified by its ability to prevent cell death. In a preferred embodiment, a method of screening a test compound for its antagonistic effect on ALK tyrosine kinase activity and potential anti-tumor activity comprises:

(a) transfecting a cell line with the NPM-ALK gene which is operably linked to a tetracycline responsive element;

(b) exposing the cells to tetracycline, resulting in activation of the NPM-ALK gene leading to cellular changes and cell death;

(c) treating a portion of the cells with a test compound either prior to, concurrently, or subsequent to, tetracycline induction of the NPM-ALK gene; and (d) monitoring cellular changes and cell death in the cultures exposed to the test compound and comparing the cellular changes and cell death in a sample of cells not treated with test compound.

As used herein, "cellular changes" refers to changes in cell size, cell shape, cell mobility, cell adhesion, or cytoskeletal changes.

The invention provides additional methods for identifying agents (e.g., chemical compounds, carbohydrates, proteins, peptides, antibodies or nucleotides) that have a growth inhibitory effect on ALK induced tumors. The invention also provides methods of identifying agents, candidate compounds or test compounds that specifically bind to ALK. Examples of agents, candidate compounds or test compounds include, but are not limited to, nucleic acids (e.g., DNA and RNA), carbohydrates, lipids, proteins, peptides, peptidomimetics, small organic molecules and other drugs. Agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

In one embodiment, agents that interact with (i.e., bind to) NPM-ALK or a polypeptide or fragment (e.g. a functionally active fragment), are identified in a cell-based assay system. In accordance with this embodiment, cells expressing NPM-ALK comprising an NPM-ALK peptide or polypeptide, a fragment thereof, are contacted with a candidate compound or a control compound and the ability of the candidate compound to interact with NPM-ALK is determined. If desired, this assay may be used to screen a plurality (e.g., a library) of candidate compounds. The cell, for example, can be of prokaryotic origin (e.g., E. coli), and may contain the NPM-ALK peptide or polypeptide, fragment, or related polypeptide thereof. In some embodiments, the NPM-ALK or NPM-ALK polypeptide, fragment, or related polypeptide thereof or the candidate compound is labeled, for example with a radioactive label (such as $^{32}$P, $^{35}$S or $^{125}$I) or a fluorescent label (such as fluorescein isothiocyanate, rhodamine, phycoerythrin, phycocyanin, allophycocyanin, o-phthaldehyde or fluorescamine) to enable detection of an interaction between a NPM-ALK and a candidate compound. The ability of the candidate compound to interact directly or indirectly with the NPM-ALK can be determined by methods known to those of skill in the art. For example, the interaction can be determined by flow cytometry, a scintillation assay, immunoprecipitation or western blot analysis.

In another embodiment, agents interact with (i.e., bind to) NPM-ALK in a cell-free assay system. In accordance with this embodiment, NPM-ALK is contacted with a candidate compound or a control compound and the ability of the candidate compound to interact with the NPM-ALK is determined. If desired, this assay may be used to screen a plurality (e.g. a library) of candidate compounds. In one embodiment, the NPM-ALK is first immobilized, by, for example, contacting the NPM-ALK with an immobilized antibody which specifically recognizes and binds it, or by contacting a purified preparation of the NPM-ALK with a surface designed to bind proteins. The NPM-ALK may be partially or completely purified (e.g., partially or completely free of other polypeptides) or part of a cell lysate.

In another embodiment, inhibitors of NPM-ALK expression or activity are identified using beads containing an NPM-ALK substrate for phosphorylation, followed by incubation of these beads with $^{32}$P-ATP plus or minus the potential inhibitor/antagonist. Determination of the levels of $^{32}$P radioactivity on the bead is used as a readout of kinase activity or inhibition thereof. Although this method can be used for screening for novel inhibitors/antagonists, adaptation of this method for use in high-throughput screening is envisioned.

In another embodiment, agents that interact with (ie. bind to) and subsequently inhibit the activity of the ALK tyrosine kinase may be identified by measuring the ability of these potential antagonists to inhibit phosphorylation of ALK in cells that harbor the ALK gene, or to measure the ability of a test compound to prevent phosphorylation of downstream molecules by the ALK tyrosine kinase. Non-limiting examples of these downstream molecules may include Shc, IRS-1, Grb-2, PI3K, Stat and Jak.

In another embodiment, the ALK or NPM-ALK gene product may be crystallized in the presence or absence of potential antagonists. Crystallographic analysis may aid in the identification of the active binding site for the antagonist. The results of such analysis may further aid in identification of other more specific or more active ALK antagonists based on mapping of the active binding site.

In another embodiment, agents that competitively interact with (i.e., bind to) NPM-ALK are identified in a competitive binding assay. In accordance with this embodiment, cells containing NPM-ALK are contacted with a candidate compound and a compound known to interact with the NPM-ALK, and the ability of the candidate compound to competitively interact with the NPM-ALK is then determined. Alternatively, agents that competitively interact with (i.e., bind to) NPM-ALK are identified in a cell-free assay system by contacting the NPM-ALK with a candidate compound and a compound known to interact with NPM-ALK. As stated above, the ability of the candidate compound to interact with NPM-ALK can be determined by methods known to those of skill in the art. These assays, whether cell-based or cell-free, can be used to screen a plurality (e.g., a library) of candidate compounds.

In another embodiment, agents that modulate (i.e., up-regulate or down-regulate) the activity of NPM-ALK are identified by contacting cells (e.g., cells of prokaryotic or eukaryotic origin) containing the components capable of forming an active NPM-ALK with a candidate compound or a control compound (e.g., phosphate buffered saline (PBS)) and determining the activity of the NPM-ALK. The level of NPM-ALK activity in the presence of the candidate compound is compared to the level of activity in the absence of the candidate compound (e.g., in the presence of a control compound). The candidate compound can then be identified as a modulator of the activity of the NPM-ALK based on this comparison. For example, when presence of an active NPM-ALK is significantly greater in the presence of the candidate compound than in its absence, the candidate compound is identified as a stimulator of NPM-ALK activity. Alternatively, when presence of an active NPM-ALK is significantly less in the presence of the candidate compound than in its absence, the candidate compound is identified as an inhibitor of NPM-ALK activity.

In another embodiment, agents that modulate the activity of an active NPM-ALK molecule are identified by contacting a preparation containing NPM-ALK, or cells (e.g., prokaryotic or eukaryotic) forming an active NPM-ALK with a test compound or a control compound and determining the ability of the test compound to modulate (e.g., stimulate or inhibit) the activity of the NPM-ALK. The activity of the NPM-ALK can be assessed in a number of ways, known to those skilled in the art.

In another embodiment, agents that modulate (i.e., up-regulate or down-regulate) NPM-ALK are identified in an animal model. Examples of suitable animals include, but are not limited to, mice, rats, rabbits, monkeys, guinea pigs, dogs and cats. Preferably, the animal used represents a model of an NPM-ALK-associated disease or condition, such as those cancers known to be associated with ALK tyrosine kinase. Examples of such cancers may be anaplastic large cell lymphomas (ALCL), T cell lymphomas, B cell lymphomas and multiple myeloma.

In accordance with this embodiment, the test compound or a control compound is administered (e.g., topically, orally, rectally or parenterally such as intraperitoneally or intravenously) to a suitable animal and the effect on the activity of the NPM-ALK is determined, or the effect on an NPM-ALK-bearing target cell is determined. Changes in the activity of NPM-ALK can be assessed by any suitable method described above, based on the present description.

The ability of the candidate compound to interact with the NPM-ALK can be determined by other methods known to those of skill in the art.

This invention further provides novel agents identified by the above-described screening assays and uses thereof for treatments as described herein.

Therapeutic Uses of the Invention

Another aspect of the invention provides for the use of ALK inhibitors in prevention of tumor growth in vivo. Evidence for the effects of such ALK inhibitors on inhibition of tumor growth are demonstrated herein. One embodiment of the invention features use of the inhibitors to prevent growth of cancers induced by ALK tyrosine kinase. The inhibitors of ALK activity are envisioned to be small molecule inhibitors, peptides, polypeptides, antibodies, antibody fragments or mimics thereof.

The invention provides for treatment or prevention of various diseases and disorders by administration of a therapeutic agent. Such agents include but are not limited to agents which prevent expression and/or activity of the ALK gene product, agents which modulate the activity of ALK, agents able to act as antagonists of ALK, and related analogs, derivatives, and fragments thereof. Such antagonists may include small molecule inhibitors or antibodies to ALK.

In one embodiment wherein inhibition of ALK is desirable, one or more inhibitors, each specifically binding to the ALK, are administered alone or in combination with one or more additional therapeutic compounds or treatments. In a preferred embodiment, an ALK inhibitor is administered to a human subject for cancer therapy.

Assays for Therapeutic Compounds

The present invention also provides for assays for use in discovery of pharmaceutical products in order to identify or verify the efficacy of compounds for treatment or prevention of NPM-ALK-mediated cancers. In one embodiment, agents can be assayed for their ability to inhibit tumor growth in vitro or in vivo. Compounds able to reduce NPM-ALK activity in vitro can be further tested for anti-tumor activity in experimental animal models of cancer and can be used as lead compounds for further drug discovery, or used therapeutically.

In various embodiments, in vitro assays can be carried out with cells that harbor the NPM-ALK gene and that are representative of the tumor cell type involved in a subject's disease, to determine if a compound has a desired effect upon such tumor cell types. In one embodiment, the cells are T or B cell lymphomas, anaplastic large cell lymphomas, or multiple myelomas.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. In one embodiment, test compounds that modulate the formation or activity of NPM-ALK are identified in non-human animals (e.g., mice, rats, monkeys, rabbits, and guinea pigs), preferably non-human animal models for NPM-ALK-associated cancers. In accordance with this embodiment, a test compound or a control compound is administered to the animals, and the effect of the test compound on NPM-ALK levels or activity is determined in the tumor obtained from the infected animal. A test compound that alters the level or activity of NPM-ALK can be identified by comparing the level of the selected NPM-ALK in a tumor cell culture obtained from an animal or group of animals treated with a test compound with the level of the NPM-ALK in a tumor culture obtained from an animal or group of animals treated with a control compound, or no compound.

In yet another embodiment, test compounds that modulate the level or activity of ALK are identified in human subjects having a tumor that contains the ALK gene. In accordance with this embodiment, a test compound or a control compound is administered to the human subject, and the effect of a test compound on either reduction in size of the tumor, elimination of the tumor or amelioration of symptoms associated with the tumor or cancer is determined by methods known in the art.

siRNA Therapy

In general terms, RNA interference (RNAi) is the process whereby the introduction of double stranded RNA into a cell inhibits the expression of a gene corresponding to its own sequence. RNAi is usually described as a post-transcriptional gene-silencing (PTGS) mechanism in which dsRNA triggers degradation of homologous messenger RNA in the cytoplasm. The mediators of RNA interference are 21- and 23-nucleotide small interfering RNAs (siRNA) (Elbashir, S. M., J. Harborth, W. Lendeckel, A. Yalcin, K. Weber, and T. Tuschl; (2001), Duplexes of 21-nucleotide RNAs mediate RNA interference in cultured mammalian cells. Nature 411: 494-498; Hautvágner, G., Mlynarova, L. and Nap, J. P. (2000), Detailed characterization of the posttranscriptional gene-silencing-related small RNA in a GUS gene-silenced tobacco. RNA, 6, 1445-1454). In a second step, siRNAs bind to a ribonuclease complex called RNA-induced silencing complex (RISC) that guides the small dsRNAs to its homologous mRNA target. Consequently, RISC cuts the mRNA approximately in the middle of the region paired with the antisense siRNA, after which the mRNA is further degraded[7]. A ribonuclease III enzyme, dicer, is required for processing of long dsRNA into siRNA duplexes (Bernstein, E., Caudy, A. A., Hammond, S. M. and Hannon, G. J. (2001) Role for a bidentate ribonuclease in the initiation step of RNA interference. Nature, 409, 363-366).

Mechanism of RNAi

The only RNA molecules normally found in the cytoplasm of a cell are molecules of single-stranded mRNA. If the cell finds molecules of double-stranded RNA (dsRNA), it uses a ribonuclease III enzyme, dicer, for processing of long dsRNA into siRNA duplexes (Bernstein, E., Caudy, A. A., Hammond, S. M. and Hannon, G. J. (2001) Role for a bidentate ribonuclease in the initiation step of RNA interference. Nature, 409, 363-366) containing ~22 base pairs (~2 turns of a double helix). Dicer is a bidentate RNase III, which also contains an ATP-dependent RNA helicase domain and a PAZ domain, presumably important for dsRNA unwinding and mediation of protein-protein interactions, respectively (Cerutti, L., Mian, N. and Bateman, A. (2000) Domains in gene silencing and cell differentiation proteins: the novel PAZ domain and redefinition of the piwi domain. Trends Biochem. Sci., 25, 481-482; Bernstein, E., Caudy, A. A., Hammond, S. M. and Hannon, G. J. (2001) Role for a bidentate ribonuclease in the initiation step of RNA interference. Nature, 409, 363-366). Dicer is evolutionarily conserved in worms, flies, plants, fungi and mammals (Matsuda, S., Ichigotani, Y., Okuda, T., Irimura, T., Nakatsugawa, S, and Hamaguchi, M. (2000) Molecular cloning and characterization of a novel human gene (HERNA) which encodes a putative RNA-helicase. Biochim. Biophys. Acta, 1490, 163-169), and has a second cellular function important for the development of these organisms (Ray, A., Lang, J. D., Golden, T. and Ray, S. (1996) Short integument (SIN1), a gene required for ovule development in Arabidopsis, also controls flowering time. Development, 122, 2631-2638); Jacobsen, S. E., Running, M. P. and Meyerowitz, M. E. (1999) Disruption of an RNA helicase/RNase III gene in Arabidopsis causes unregulated cell division in floral meristems. Development, 126, 5231-5243; Grishok, A. et al. (2001) Genes and mechanisms related to RNA interference regulate expression of the small temporal RNAs that control C. elegans developmental timing. Cell, 106, 23-34; Hutvagner, G., McLachlan, J., Bálint, E., Tuschl, T. and Zamore, P. D. (2001) A cellular function for the RNA interference enzyme dicer in small temporal RNA maturation. Science, 293, 834-838; Knight, S. W. and Bass, B. L. (2001) A role for the RNase III enzyme DCR-1 in RNA interference and germ line development in C. elegans. Science, 293, 2269-2271). At present, it is uncertain whether dicer activity in species other than D.melanogaster produces siRNAs of predominantly 21 nt in length. The estimates of siRNA size vary in the literature between 21 and 25 nt (Hamilton, A. J. and Baulcombe, D. C. (1999) A species of small antisense RNA in posttranscriptional gene silencing in plants. Science, 286, 950-952; Hammond, S. M., Bernstein, E., Beach, D. and Hannon, G. J. (2000) An RNA-directed nuclease mediates post-transcriptional gene silencing in Drosophila cells. Nature, 404, 293-296; Hutvágner, G., Mlynarova, L. and Nap, J. P. (2000) Detailed characterization of the posttranscriptional gene-silencing-related small RNA in a GUS gene-silenced tobacco. RNA, 6, 1445-1454; Parrish, S., Fleenor, J., Xu, S., Mello, C. and Fire, A. (2000) Functional anatomy of a dsRNA trigger: differential requirement for the two trigger strands in RNA interference. Mol. Cell, 6, 1077-1087; Yang, D., Lu, H. and Erickson, J. W. (2000) Evidence that processed small dsRNAs may mediate sequence-specific mRNA degradation during RNAi in Drosophila embryos. Curr. Biol., 10, 1191-1200; Zamore, P. D., Tuschl, T., Sharp, P. A. and Bartel, D. P. (2000) RNAi: double-stranded RNA directs the ATP-dependent cleavage of mRNA at 21 to 23 nucleotide intervals. Cell, 101, 25-33; Elbashir, S. M., Lendeckel, W. and Tuschl, T. (2001b) RNA interference is mediated by 21 and 22 nt RNAs).

The two strands of each fragment then separate enough to expose the antisense strand so that it can bind to the complementary sense sequence on a molecule of mRNA. In RNAi, a siRNA-containing endonuclease complex cleaves a single-stranded target RNA in the middle of the region complementary to the 21 nt guide siRNA of the siRNA duplex. This cleavage site is one helical turn displaced from the cleavage site that produced the siRNA from long dsRNA, suggesting dramatic conformational and/or compositional changes after processing of long dsRNA to 21 nt siRNA duplexes. The target RNA cleavage products are rapidly degraded because they either lack the stabilizing cap or poly(A) tail. A protein component of the ~500 kDa endonuclease or RNA-induced silencing complex (RISC) was recently identified and is a member of the argonaute family of proteins; however, it is currently unclear whether dicer is required for RISC activity. Thus, the cleavage of the mRNA destroys its ability to be translated into a polypeptide. Because of their action, these fragments of RNA have been named "short (or small) interfering RNA" (siRNA).

Introducing dsRNA corresponding to a particular gene will knock out the cell's own expression of that gene. This can be done in particular tissues at a chosen time. This often provides an advantage over conventional gene "knockouts" where the missing gene is carried in the germline and thus whose absence may kill the embryo before it can be studied.

Although it has been suggested that the one disadvantage of simply introducing dsRNA fragments into a cell is that gene expression is only temporarily reduced, it has recently been shown that the system can be manipulated using a DNA vector such that the siRNA molecule can be continuously synthesized for prolonged periods of time in order to continue in suppression of the desired gene (Brummelkamp et. al. 19 Apr. 2002, Science). After two months, the cells still failed to manufacture the protein whose gene had been turned off by RNAi. Effective siRNA molecules may be designed using the following guidelines:

In general, siRNA oligonucleotides should be about 21 nucleotides in length with 2 nucleotide overhangs, usually 3' TT.

The target sequence should be located approximately 50 to 100 nucleotides downstream of the AUG start codon.

Sequences located in the 5' or 3' UTR of the mRNA target and nearby the start codon should be avoided, as they may be richer in regulatory protein binding sites.

Search for a sequence AA(N19)TT or AA(N21) with approximately 50% G/C content.

Compare the selected siRNA nucleotide sequence against databases to ensure that only one gene will be targeted.

Target recognition is a highly sequence specific process, mediated by the siRNA complementary to the target. One or two base pair mismatches between the siRNA and the target gene will greatly reduce the silencing effect. It might be necessary to test several sequences since positional effects of siRNAs have been reported.

The 3'-most nucleotide of the guide siRNA does not contribute to the specificity of target recognition, while the penultimate nucleotide of the 3' overhang affects target RNA cleavage and a mismatch reduces RNAi 2- to 4-fold. The 5' end of the guide siRNA also appears more permissive for mismatched target RNA recognition when compared with the 3' end. Nucleotides in the center of the siRNA, located opposite to the target RNA cleavage site, are important specificity determinants and even single nucleotide changes reduce RNAi to undetectable levels. This suggests that siRNA duplexes may be able to discriminate mutant or polymorphic alleles in gene targeting experiments, which may become an important feature for future therapeutic developments.

Gene Therapy and Transgenic Vectors

A gene encoding an inhibitor of ALK tyrosine kinase or an active fragment thereof, derivative thereof, or structural/functional domain thereof, can be introduced either in vivo, ex vivo, or in vitro in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. For example, in the treatment of cancers associated with ALK tyrosine kinase, the tumor cell may be specifically targeted. Examples of particular vectors include, but are not limited to, a defective herpes virus 1 (HSV1) vector (Kaplitt et al., *Molec. Cell. Neurosci.*, 2:320-330 (1991)), an attenuated adenovirus vector, such as the vector described by Stratford-Perricaudet et al. (*J. Clin. Invest.*, 90:626-630 (1992)), and a defective adeno-associated virus vector (Samulski et al., *J. Virol.*, 61:3096-3101 (1987); Samulski et al., *J. Virol.*, 63:3822-3828 (1989)) including a defective adeno-associated virus vector with a tissue specific promoter, (see e.g., U.S. Pat. No. 6,040,172, Issued Mar. 21, 2000, the contents of which are hereby incorporated by reference in their entireties).

In another embodiment the ALK inhibitor, can be introduced in a retroviral vector, e.g., as described in U.S. Pat. No. 5,399,346; Mann et al., (1983) Cell, 33:153; U.S. Pat. No. 4,650,764; U.S. Pat. No. 4,980,289; Markowitz et al., (1988) J. Virol., 62:1120; U.S. Pat. No. 5,124,263; International Patent Publication No. WO 95/07358, published Mar. 16, 1995; and Kuo et al., (1993) Blood, 82:845.

Targeted gene delivery is described in International Patent Publication WO 95/28494, published October 1995.

Non-limiting examples of techniques which can be used to introduce an expression vector encoding an ALK tyrosine kinase inhibitor into a host cell include the following:

Adenovirus-Polylysine DNA Complexes: Naked DNA can be introduced into cells by complexing the DNA to a cation, such as polylysine, which is then coupled to the exterior of an adenovirus virion (e.g., through an antibody bridge, wherein the antibody is specific for the adenovirus molecule and the polylysine is covalently coupled to the antibody) (see Curiel, D. T., et al. (1992) Human Gene Therapy 3:147-154). Entry of the DNA into cells exploits the viral entry function, including natural disruption of endosomes to allow release of the DNA intracellularly. A particularly advantageous feature of this approach is the flexibility in the size and design of heterologous DNA that can be transferred to cells.

Receptor-Mediated DNA Uptake: Naked DNA can also be introduced into cells by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967; and U.S. Pat. No. 5,166,320). Binding of the DNA-ligand complex to the receptor facilitates uptake of the DNA by receptor-mediated endocytosis. Receptors to which a DNA-ligand complex have targeted include the transferrin receptor and the asialoglycoprotein receptor. Additionally, a DNA-ligand complex can be linked to adenovirus capsids which naturally disrupt endosomes, thereby promoting release of the DNA material into the cytoplasm and avoiding degradation of the complex by intracellular lysosomes (see for example Curiel et al. (1991) Proc. Natl. Acad. Sci. USA 88:8850; and Cotten, M. et al. (1992) Proc. Natl. Acad. Sci. USA 89:6094-6098; Wagner, E. et al. (1992) Proc. Natl. Acad. Sci. USA 89:6099-6103). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Liposome-Mediated transfection ("lipofection"): Naked DNA can be introduced into cells by mixing the DNA with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) Meth. Enz. 149:157-176; Wang and Huang (1987) Proc. Natl. Acad. Sci. USA 84:7851-7855;

Brigham et al. (1989) Am. J. Med. Sci. 298:278; and Gould-Fogerite et al. (1989) Gene 84:429-438.

Direct Injection: Naked DNA can be introduced into cells by directly injecting the DNA into the cells. For an in vitro culture of cells, DNA can be introduced by microinjection, although this not practical for large numbers of cells. Direct injection has also been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo can be used. Such an apparatus is commercially available (e.g., from BioRad).

Retroviral Mediated Gene Transfer: Defective retroviruses are well characterized for use in gene transfer for gene therapy purposes (for a review see Miller, A. D. (1990) Blood 76:271). A recombinant retrovirus can be constructed having a nucleic acid encoding a gene of interest (e.g., an ALK inhibitor) inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE, pEM and lentivirus, which are well known to those skilled in the art.

Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Adenoviral Mediated Gene Transfer: The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to many other gene delivery vectors (Berkner et al. cited supra; Haj-Ahmand and Graham (1986) J. Virol. 57:267). Most replication-defective adenoviral vectors currently in use are deleted for all or parts of the viral E1 and E3 genes but retain as much as 80% of the adenoviral genetic material.

Adeno-Associated Viral Mediated Gene Transfer: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of the introduced DNA can be detected, for example, by Northern blotting, RNase protection or reverse transcriptase-polymerase chain reaction (RT-PCR). Expression of the introduced gene product in the cell can be detected by an appropriate assay for detecting proteins, for example by immunohistochemistry.

As will be appreciated by those skilled in the art, the choice of expression vector system will depend, at least in part, on the host cell targeted for introduction of the nucleic acid. For example, nucleic acid encoding an inhibitor of ALK tyrosine kinase, for example, an antibody to ALK tyrosine kinase, which blocks expression of ALK tyrosine kinase is preferably introduced into tumor cells showing enhanced proliferative capacity and highly invasive characteristics. Tumor cells that are responsive to treatment with the inhibitors or blocking antibodies of the present invention include tumors of T and B cell origin. Preferred expression vectors and delivery systems for introducing nucleic acid into malignant cells include transfection with adenoviral-polylysine DNA complexes and adenoviral vector-mediated gene transfer. Alternatively, in the case where the inhibitor is an antisense nucleic acid molecule or an siRNA molecule, the preferred mode of delivery is by way of a lentivirus vector system. These delivery systems are suitable for introduction of nucleic acid into cells in vitro, or more preferably for tumor cells, in vivo.

The functional outcome of delivery of the antisense or siRNA molecule, on the subsequent expression and/or function of the protein targeted for inhibition (referred to as the target protein, in this case, ALK), can be assessed by suitable assays that monitor the expression and/or function of the target protein, including standard immunohistochemistry or immunoelectron microscopy techniques.

Alternatively, cell proliferation can be measured using commercially available cell proliferation assays. The functional outcome of inhibition of ALK expression on tumor cell growth and survival in a mammal can be assessed in vivo using animal model systems that may be predictive of therapeutic efficacy in humans. For example, the inhibitor nucleic acid may be inserted into a human cancer cell known to express the ALK tyrosine kinase gene. These cells may be implanted into athymic nude mice, and tumor growth may be monitored visually over time.

Furthermore, if the inhibitory molecule specific for ALK tyrosine kinase is an antisense nucleic acid or a small interfering RNA molecule, the vectors may be selected from a retrovirus such as for example, a human immunodeficiency virus type 1-derived lentivirus vector. While any retrovirus may be utilized, the lentivirus approach allows for delivery to a broad variety of cellular targets, both ex vivo (cell lines, primary cells including stem cells, fertilized oocytes, and blastocysts) and in vivo (e.g., brain and liver). The lentivirus vector-mediated delivery of siRNAs allows for the controllable suppression of cellular genes both with a high degree of efficacy and without significant leakiness. Alternatively, a virus which enters the mammalian cell via a specific receptor may be used, such as, but not limited to Sindbis virus. In this situation, the gene encoding the receptor may be replaced with a gene encoding for example, CD30 ligand. Since the CD30 receptor is expressed on tumor cells expressing ALK tyrosine kinase, the ALK inhibitor can be incorporated into Sindbis virus which has been genetically modified to express the CD30 ligand and thus can be delivered specifically to the tumor cell.

Alternatively, the vector can be introduced by lipofection. Liposomes may be used for encapsulation and transfection of nucleic acids in vitro. Synthetic cationic lipids designed to limit the difficulties and dangers encountered with liposome mediated transfection can be used to prepare liposomes for in vivo transfection of a gene encoding an inhibitor of ALK tyrosine kinase (Felgner, et. al., *Proc. Natl. Acad. Sci. U.S.A.*, 84:7413-7417 (1987); see Mackey, et al., *Proc. Natl. Acad. Sci. U.S.A.*, 85:8027-8031 (1988)). The use of cationic lipids may promote encapsulation of negatively charged nucleic acids, and also promote fusion with negatively charged cell membranes (Felgner and Ringold, *Science*, 337:387-388 (1989)). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as the brain. Lipids may be chemically coupled to other molecules for the purpose of targeting (see Mackey et. al., *Proc. Natl. Acad. Sci. U.S.A.*, 85:8027-8031 (1988)).

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., (1992) *J. Biol. Chem.*, 267:963-967; Wu and Wu, (1988) *J. Biol. Chem.*, 263:14621-14624; Hartmut et al., Canadian Patent Application No. 2,012,311, filed Mar. 15, 1990).

In a preferred embodiment of the present invention, a gene therapy vector as described above employs a transcription control sequence operably associated with the nucleotide sequence encoding the ALK inhibitor inserted in the vector. That is, a specific expression vector of the present invention can be used in gene therapy.

Such an expression vector is particularly useful to regulate expression of a therapeutic ALK inhibitor gene. A regulatable promoter may also be used.

In a particular embodiment, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-(IFN), or anti-CD4 antibody, can be administered to block humoral or cellular immune responses to the viral vectors (see, e.g., Wilson, *Nature Medicine*, (1995)). In addition, it is advantageous to employ a viral vector that is engineered to express a minimal number of antigens.

Therapeutic and Prophylactic Compositions and Their Use

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject.

Various delivery systems are known and can be used to administer a compound of the invention, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment, such as topical use on the skin; any suitable method known to the art may be used.

Another aspect of the invention provides for pharmaceutical compositions comprising purified NPM-ALK inhibitors for therapeutic use in treatment of cancers. One embodiment features treatment of a wide range of cancers including lymphoid tumors including but not limited to T or B cell lymphomas, anaplastic large cell lymphomas, or multiple myelomas with pharmaceutical compositions containing acceptable carriers and excipients. Moreover, a further embodiment may include a pharmaceutical composition designed for use in topical treatment of skin cancers. Another embodiment may include a pharmaceutical composition designed for use in treatment of systemic or other lymphoid cancers, or cancers that are non-responsive to other treatment modalities.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the compound of the invention which will be effective in the treatment of cancers wherein the tumor contains the ALK gene can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872-10876). In one embodiment, administration can be by direct injection by aerosol inhaler.

In another embodiment, the inhibitor compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.)

In yet another embodiment, the inhibitor compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

EXAMPLES

The following examples are put forth so as to provide those of ordinary skill in the art with a complete disclosure and description of how to prepare and use the novel transgenic animal model for the study of cancers associated with expression and/or activity of the ALK tyrosine kinase described herein, and to provide a suitable means for identifying and assaying appropriate inhibitors of this protein and development of pharmaceutical compositions for therapeutic use, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of NPM-ALK Tg Mice, Cell Lines and Statistical Analysis

Preparation of Transgenic Mice

NPM-ALK transgenic mice were generated by injecting Swiss-Webster blastocysts with a construct in which the full length cDNA of NPM-ALK chimera was placed under the control of the murine CD4 promoter. The transgenic cassette (CD4 cassette) included the minimal CD4 enhancer (339 bp), the minimal murine CD4 promoter (487 bp), the transcription initiation site, and 70 bp of the untranslated first exon and part of the first intron of the murine CD4 gene but lacked the CD8 silencer (Sawada, S. et al. (1994) Cell. 77:917-929). The NPM-ALK founders were back-crossed into Balb/c and C57B/6 strains and housed in a germ-free facility (Skirball Institute of Biomolecular Medicine, New York University School of Medicine). Positive NPM-ALK mice were detected by PCR using genonic DNA obtained from mouse tail biopsies as previously described (Chiarle, R. et al. (1999) J. Immunol. 163:194-205). All experiments presented in this study were derived from mice (C57BL/6 and Balb/c backgrounds) obtained from two independent transgenic lines (N1 and N16). cul1 Tg mice were obtained placing (SacI/SalI) the human Cul1-N252 cDNA (encoding 1 to 252 (N252) amino terminal residues) into the CD4 cassette Tg (Piva, R. et al. Molecular and Cellular Biology. In press). Screening of founder animals and their corresponding offspring was performed by PCR and confirmed by Southern hybridization on genomic DNA from tail biopsies. Rag2−/− mice were purchased from Taconic (Taconic, Germantown, N.Y.). The DHL cell line was a gift of Dr. Lorenzana. Primary NPM-ALK cells were obtained from fresh thymic tumors after being cultured in complete RPMI-1640 medium in vitro. Survival curves were performed using the non-parametric model of Kaplan-Meyer.

Immunoprecipitation and Western Blot analysis

Tissue samples and cell lines were lysed (50 mM Tris-HCl pH7.4, 150 mM NaCl, 0.1% Triton X100, 5 mM EDTA, 1 mM $Na_3VO_4$ and 1 mM PMSF and protease inhibitors) and supernatants were then used for immunoprecipitation and Western Blotting analysis. For immunoprecipitations, 0.2-0.5 mg of total proteins were incubated for 1 hr at 4° C. with 3 µg of rabbit anti-ALK antibody (Ab) or a cocktail of mouse anti-ALK Mabs (Zymed, South San Francisco, Calif.), or with anti-Grb-2 Ab (Santa Cruz Biotechnology, Santa Cruz, Calif.), anti-PI3K Ab (UBI Biotechnology, Waltham, Mass.), then 30 µl of protein G-sepharose beads (1:1) were added for 30 minutes. Immunocomplexes were washed (3 times with the lysis buffer) and subsequently loaded onto a SDS-PAGE gel. For Western blotting, 30 µg of proteins were run in SDS-PAGE gels and transferred onto nitrocellulose membranes. Membranes were blocked (5% low fat milk in PBS with 0.1% Tween 20; 1 hour at RT) and subsequently incubated with the primary antibodies for 1 hr at room temperature {rabbit anti-ALK (1:4000, Zymed), mouse anti-ALK Mab (1:5000, Zymed), anti-phosphotyrosine (1:1000, Transduction Lab-Becton-Dickinson, Mountain View, Calif.), anti-Stat3 Mab (1:1000, Zymed), anti-Jak-1, Jak2, Jak3, Tyk-2 Ab (1:500, Zymed), anti-Shc Ab (1:500, Santa Cruz). Filters were washed three times and then incubated with HRPO-conjugated goat anti-mouse or anti-rabbit (1:2000, Amersham, Arlington Heights, Ill., 1 hour at RT) antibodies. Immunocomplexes were detected by using a chemiluminescence system (ECL, Amersham, Piscataway, N.J.) (Chiarle, R. et al. (2000) Blood. 95:619-626).

Southern Blotting

Southern blotting was performed as previously described (Chiarle, R. et al. (1999) J. Immunol. 163:194-205). Briefly, high molecular weight genomic DNAs (10 g) were digested by EcoRI, Hind III, or Pvu endonucleases and then digested fragments were separated by electrophoresis. DNAs were subsequently transferred onto nitrocellulose. Radiolabeled cDNA probes were used to study the genomic configuration of TCR and heavy chain immunoglobulin loci (Mangues, R. et al. (1996) Oncogene. 13:1053-1063). Human NPM-ALK genomic sequences were investigated using BamHI digested DNAs using a specific ALK cDNA probed (BamHI-BamHI).

Flow Cytometry, Histology and Immunohistochemistry

Single cell suspensions were obtained from isolated tissue samples. Cells were washed, counted and stained with the following murine primary FITC-, PE- or Tricolor-conjugated antibodies: Thy-1, CD4, CD8, B220, CD25, CD3, TCR, TCR (Caltag Laboratories, Burlingame, Calif.), CD30, CD44, and CD45RB (Pharmingen-BD Biosciences, San Josè, Calif.). After staining (30 m at 4° C.), cells were washed and analyzed using a FACScan (Becton-Dickinson) flow cytometer as described (Chiarle, R. et al. (1999) J Immunol. 163:194-205). For the histological and immunohistochemistry analyses, tissue samples were fixed in PBS-buffered formalin (10%) and subsequently embedded in paraffin. De-waxed 4 m thick tissue sections were stained with Hematoxylin and Eosin or after microwave retrieval (citrate buffer, pH6.6, 15 min) incubated with anti-ALK primary antibody (1:1000, Zymed), anti-Ki-67 (Novacastro), anti-CD45R (1:100, Caltag) and anti-CD138 (1:20, Pharmingen-BD). Bound complexes were revealed using the avidin biotin peroxidase complex and a semi-automated immunostainer (DAKO, Carpinteria, Calif. or Ventana ES Medical Systems, Tucson, Ariz.). Mouse light and heavy chain expression was performed using alkaline conjugated rabbit anti-mouse antibodies Southern Biotechnology Associates, Inc., Birmingham, Ala.). For immunofluorescence stains, paraffin embedded tissue sections were treated as described above. Sections were then incubated with rabbit anti-ALK Ab. After washing, tissue sections were incubated with biotin-conjugated anti-rabbit Ab (1:200, Vector) and then FITC-Avidin (1:200, Sigma, Sigma-Aldrich Corporation, St. Louis, Mo.). Sections were subsequently incubated with normal rabbit serum (1:10, 30 minutes at RT) and then stained with PE conjugated anti-B220 (1:20, Caltag) in presence of rabbit serum (1:10). After washing, slides were briefly dried and coverslipped with anti-fade (Vysis, Downers Grove, Ill.). Flourescence staining was visualize using the 2.7 Cytovision software (Applied Imaging, Santa Clara, Calif.).

Tissue Culture

The rate of spontaneous and in vitro induced cell death was evaluated based on DNA content and propidium iodide or Annexin-V (Pharmingen-BD) stainings (Chiarle, R. et al. (1999) J Immunol. 163:194-205). Briefly, thymocytes were cultivated with immobilized anti-CD3 antibody (10 g/ml, 2C11, a gift of J. Bluestone) and soluble anti-CD28 antibody (5 g/ml, Pharmingen-BD). Alternatively thymocytes were cocultured with dexamethazone (0.1 M), TNF (15 ng/ml), cycloheximide (75 g/ml Sigma), anti-Fas Ab (0.5 g/ml, Pharmingen-BD), PMA (10 ng/ml, Sigma) or Ionomycin (1 M, Sigma). At the indicated times, cells were harvested, washed and stained.

Purified peripheral T cells were obtained by magnetic-beads separation. Briefly, $1 \times 10^7$ lymph node cells were first incubated (for 30 min at room temperature) with a cocktail of antibodies (0.2-0.5 g each antibody/$10^6$ cells) against B cells (B220, Caltag), macrophages (CD11c, Caltag) and NK cells (Anti-NK, Caltag). At the end of incubation, 70 l of anti-rat conjugated magnetic beads (Dynabeads, Dynal, Lake Success, N.Y.) were added. Bead-coated cells were separated in a magnetic field and unbound cells were washed in cold PBS (3×). Negatively selected T cells were first stained with FITC-conjugated anti-CD3 mAb and analyzed by FACS to determine their purity (always greater than 95%). Highly purified T cells ($5 \times 10^4$) were cultivated in RPMI-1640 medium supplemented with 10% FCS and streptomycin and penicillin and $10^{-5}$ M 2-mercaptoethanol in 96 well plate coated with anti-CD3 (0.1 to 10 g/ml) and soluble anti-CD28 (0.5 g/ml) antibody for 48 hours. Alternatively purified T cells were cocultured with PMA (10 ng/ml) or ConA (5 g/ml). $^3$H-thymidine (1 Cu/well; New England Nuclear, Boston, Mass.) was added for the last 18 hours of culture. Cells were harvested and counted in a Beta-counter.

Electrophoretic Methods

Semiatutomated agarose electrophoresis and immunofixation were performed on Sebia's HYDRASYS and HYRYS systems (Sebia Inc., Norcross, Ga., USA) according to the manufacturer's instructions. For protein electrophoresis, 10 μl of sample were applied manually to the sample template. The subsequent sample application, electrophoresis (pH 8.6, 20 W, at 20° C.), gel drying and staining were performed automatically. The resulting electrophoretic profiles were scanned employing the Hyris densitometer (Sebia). For immunofixation, each sample was applied in six different positions on agarose gels (Hydragel Immunofixation, Sebia) and the electrophoretic separation performed automatically under identical conditions as above. Either fixative or monospecific antisera to mouse immunoglobulins (kappa, lambda, IgG, IgM, and IgA; Southern Biotechnology Associates, Inc.) were applied to the electrophoresis lanes to allow for fixation and immunoprecipitation, respectively. Detection of monoclonal bands was assessed by visual inspection of stained gels.

Results

NPM-ALK is Expressed in Normal T Cells

To study the influence of NPM-ALK in T cells of mice, the full length cDNA of NPM-ALK fusion gene was cloned in a vector under the control of the CD4 promoter (FIG. 1a). Injection of this construct into blastocysts yielded six different NPM-ALK founders that were identified from three foster mothers. The copy number of the NPM-ALK trangene varied considerably among the different lines (FIG. 1b). With the exception of one mouse (N8), all founders and their corresponding NPM-ALK progenies (N1, N14, N16) expressed the expected ALK fusion protein with a molecular weight of 80 kDa (FIG. 1c). This protein corresponded to the NPM-ALK of human cell lines carrying the t(2; 5) translocation and was expressed at levels similar to those of human ALCL-derived cell lines (FIG. 1c). All five NPM-ALK expressing founders were crossed to generate five different mouse lines. However, N5 and N15 died, before mating, of bilateral posterior limb paralysis and thymic tumor, respectively.

The CD4 transgene cassette allows the expression of the target protein in all T cells, including early progenitor thymocytes (CD4+/CD8+) and single positive T cells (CD4+/CD8− and CD4−/CD8+) (Chiarle, R. et al. (1999) J Immunol. 163:194-205). As predicted, the transgenic NPM-ALK protein was localized to cortical and medullary thymocytes, lymphocytes within the interfollicular areas of lymph nodes and in the T cell areas of the splenic white pulp (FIG. 1d). NPM-ALK was detected in the cytoplasm and nucleus, a pattern similar to that observed in human NPM-ALK positive cells.

Stat3 and Jak3 are Constitutively Phosphorylated in NPM-ALK Tg Mice

Figure 2:
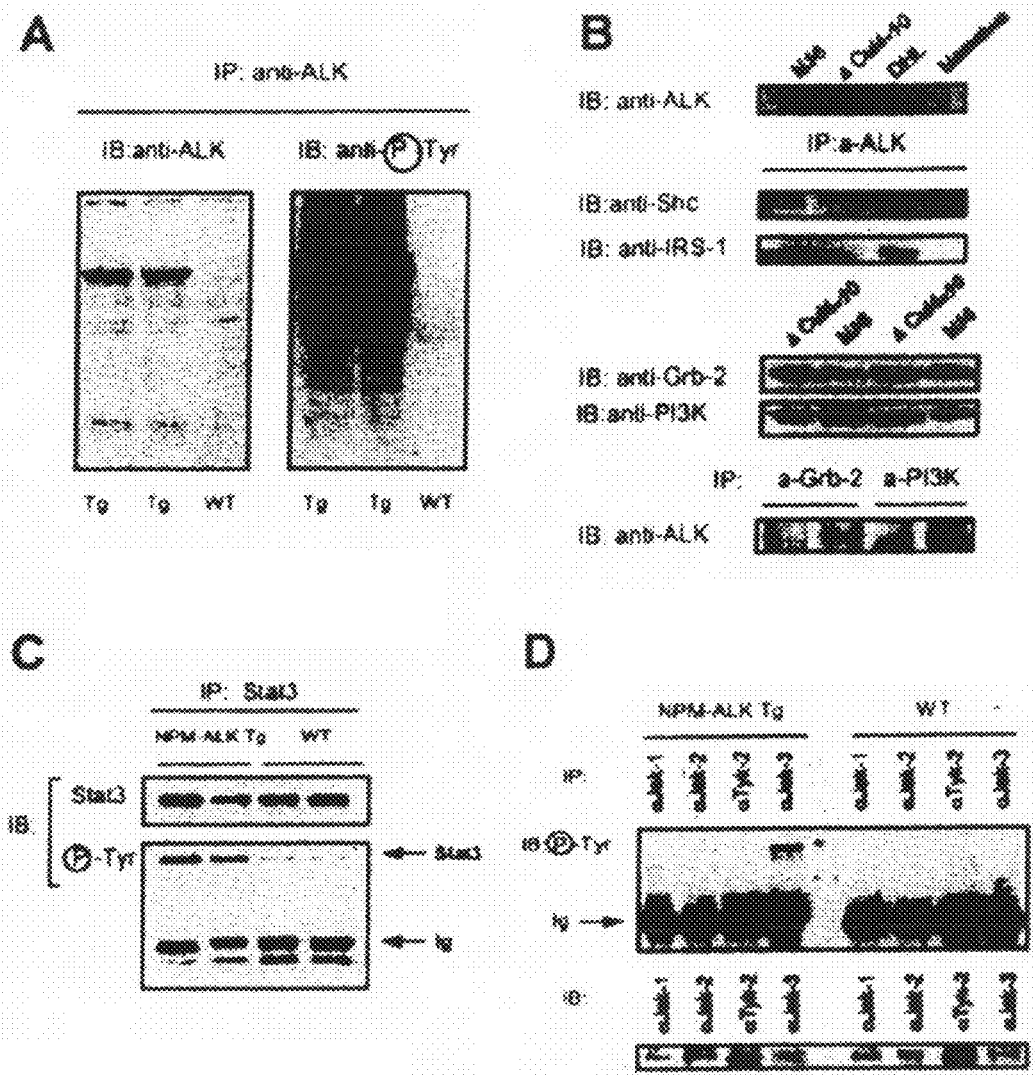
FIG. 2. Molecular characterization of NPM-ALK Tg mice. (A) Expression and constitutive activation of NPM-AK in Tg mice. Thymocytes from Tg and WTmice were lysed and immunoprecipitated with anti-ALK Ab as described herein. Western blot with anti-ALK revealed the presence of the protein in Tg but not WT mice (left panel). NPM-ALK protein was constitutively phosphorylated in Tg mice as revealed by the antiphosphotyrosine Ab (right panel). (B) NPM-ALK protein expressed in murine T cells coprecipitates with Shc, IRS-1, Grb-2, and PI3K. Lysates from ALK samples were immunoprecipitated with anti-ALK (upper panel) or with anti-Grb-2 or anti-PI3K (lower panel). Immunocomplexes were gel electrophoresed and, after transfer, incubated with the indicated antibodies. Direct Western blotting were also performed as indicated. All data are representative of at least 3 different experiments. (C)NPM-ALK Tg mice activate Stat3. Proteins extracted from Tg and WT thymocytes were immunoprecipitated with anti-Stat3 Ab and loaded onto a SDS-PAGE gel. Stat3 protein was similarly immunoprecipitated from both Tg and WT thymocytes. Antiphosphotyrosine Ab revealed the presence of higher levels of activated Stat3 in NPM-ALK Tg mice. (D) NPM-ALK Tg mice activate Jak3. Jak-family of proteins were immunoprecipitated from Tg and WTmice and detected with antiphospho-tyrosine Ab. Only Jak3 was constitutively phosphorylated in Tg but not in WT mice. The Jak-family of proteins were equally immunoprecipitated in Tg and WT mice.

Since NPM-ALK is constitutively autophosphorylated in human ALCL cells, the phosphorylation status of NPM-ALK in transgenic cells was analyzed and the results demonstrated that it was observed in normal, as well as neoplastic NPM-ALK cells, and it is constitutively phosphorylated (FIG. 2a). Because activated ALK fusion proteins can efficiently bind Shc, PLC-, Grb-2 and PI3K (Slupianek, A. et al. (2001) Cancer Res. 61:2194-2199), studies were done to determine whether the transgenic NPM-ALK fusion protein could efficiently bind the corresponding mouse proteins as well. As shown in FIG. 2b, mouse Shc, IRS-1, Grb-2 and PI3K proteins efficiently bound NPM-ALK in normal as well as in neoplastic cells. Moreover, the studies demonstrated that phosphorylated Stat3 could be coprecipitated with ALK (data not shown). Since NPM-ALK leads to the constitutive activation of Stat3 (Zhang, Q. et al. (2002) J. Immunol. 168:466-474 and Zamo, A. et al. (2002) Oncogene. 21:1038-1047) and Jak3 (Zamo, A. et al. (2002) Oncogene. 21:1038-1047), studies were done to evaluate the activation status of these molecules in the NPM-ALK Tg mice. As shown in FIG. 2c,d, NPM-ALK Tg thymocytes, but not control cells, displayed constitutively phosphorylated Stat3 and Jak3. Overall, these findings demonstrate that the NPM-ALK transgene is constitutively activated in T cells and binds to the same adaptor proteins as in humans. Thus, the transgenic model described herein mimics the molecular features of human NPM-ALK positive lymphomas.

Cellular Phenotype and Lymphoid Organ Development in NPM-ALK Transgenic Mice

Figure 3:
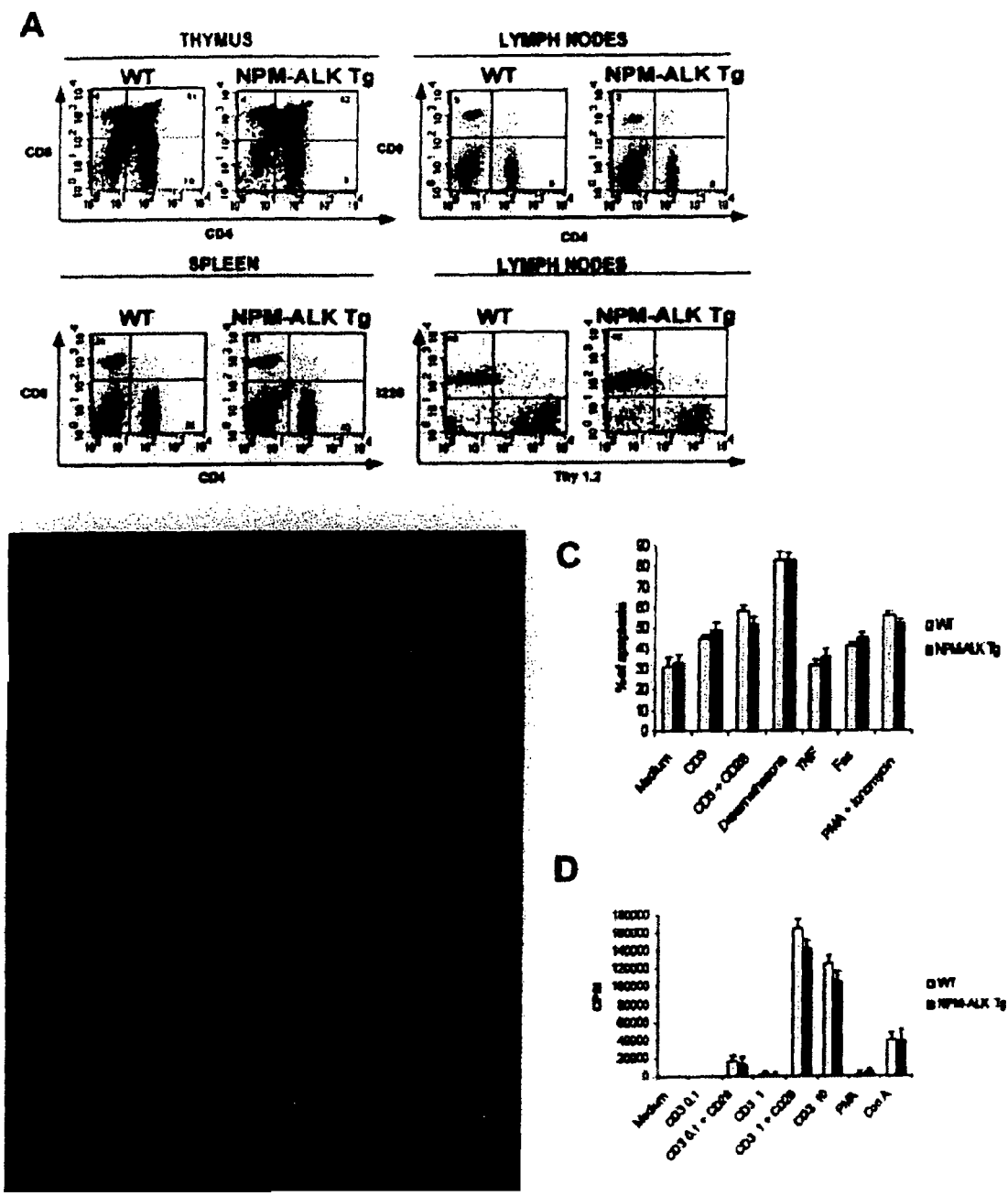
FIG. 3. Normal phenotype of NPM-ALK Tg mice. (A) Single cell suspensions obtained from thymocytes, spleen, and lymph nodes were stained with the indicated antibodies and analyzed as described herein. Tg and WT mice had comparable phenotype in both immature and mature T cells and B lymphocytes. (B) NPM-ALK expression in mature T and B lymphocytes: NPM-ALK expression is re-stricted only to T cells. Paraffin-embedded tissue section from a preoplastic of NPM-ALK Tg spleen mouse was stained with anti-ALK (green) and anti-B220 (red) Abs. Normal response of Tg lymphocytes to apoptotic and proliferative stimuli. (C) Tg and WT thymocytes were isolated and stimulated for 24 hours with the indicated reagents. The spontaneous and induced apoptotic rate was comparable in Tg and WT mice. (D) Peripheral T lymphocytes were purified from lymph nodes as described in and cultured for 72 hours in the presence of the indicated reagents. 3H-thymidine was added for the last 18 hours of culture. Proliferative responses of WT and Tg mice were comparable. The data are representative of at least 2 independent experiments.

To characterize the putative effects resulting from the constitutive activation of NPM-ALK in T lymphocytes, the morphological and phenotypic features of T cell lymphoid populations and their activation and differentiation states were analyzed. Overall, the relative and absolute numbers of T and B lymphocytes, within primary and secondary lymphoid organs, were similar in Tg and control littermate mice. Microscopic evaluation demonstrated a normal lymphoid organization with the physiological preservation of all lymphoid microenvironments. Finally, the histological surveys of lung, kidney, stomach, intestine, testis, ovaries and brain did not reveal any morphological anomalies. Flow cytometry of NPM-ALK Tg thymocytes showed a normal distribution of CD4−/CD8− and CD4+/CD8+ cells as well as of single positive CD4+ or CD8+ lymphocytes (FIG. 3a). No significant differences were observed in the expression of other T cell associated and/or restricted markers. A normal percentage and expression of V chains and/or the CD3 complexes were also documented in transgenic T lymphocytes demonstrating that T cell commitment and maturation proceed normally in these mice (data not shown). The peripheral lymphoid organs showed a normal proportion of B and T lymphocytes and a normal ratio of the CD4+ and CD8+ populations (FIG. 3a). Finally, the percentage of activated peripheral T lymphocytes was similar in Tg and WT mice as demonstrated by expression of CD25 and CD69 antigens (3-5% of the total cells). Flow cytometry of spleen showed no significant differences in the distribution of myeloid, erythroid or granulocytic lineages. Double immuno-fluorescence studies were also performed to address whether mature T and/or B cells could express NPM-ALK. As shown in FIG. 3 (Panel B), NPM-ALK expression (nuclear green staining) was restricted to B220/CD45R negative cells (B220/CD45R positive cells showed only a red membrane staining) present in the T cell areas of splenic germinal centers, suggesting that NPM-ALK was largely restricted to T lymphocytes.

To determine whether the constitutive expression of NPM-ALK could possibly modify the survival and/or proliferative potential of T lymphocytes, NPM-ALK Tg thymocytes were incubated in vitro with different apoptotic stimuli. As shown in FIG. 3c, both Tg and controls had similar rates of spontaneous and induced apoptosis. The in vitro proliferative rates of purified peripheral T-lymphocytes, stimulated with suboptimal and to "ad hoc" concentrations of mitogens, were also similar in transgenic and control mice (FIG. 3d). These findings indicate that NPM-ALK alone is not capable of significantly modifying the survival and cell growth of T lymphocytes from young mice in vitro.

NPM-ALK Transgenic Mice Develop Spontaneous Lymphoid Tumors

Figure 5:
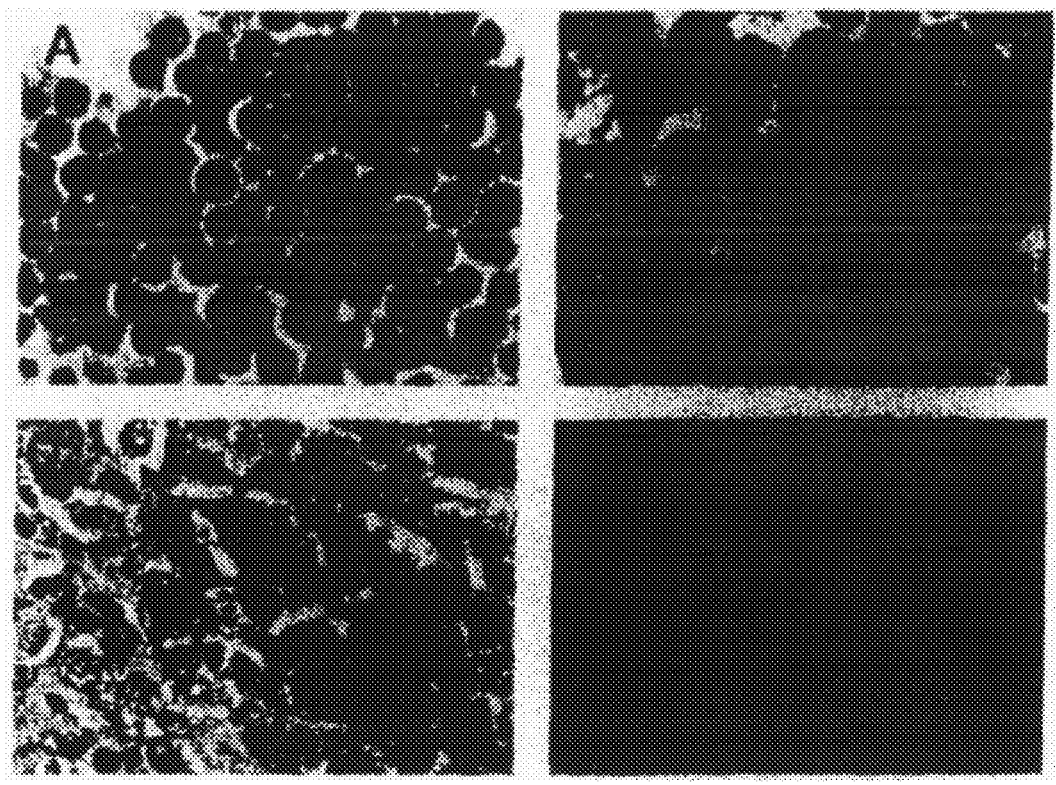
FIG. 5. NPM-ALK Tg mice develop plasma cell tumors. (A-D) Histologic sections of 4 representative plasma cell neoplasms (400×).
Figure 6:
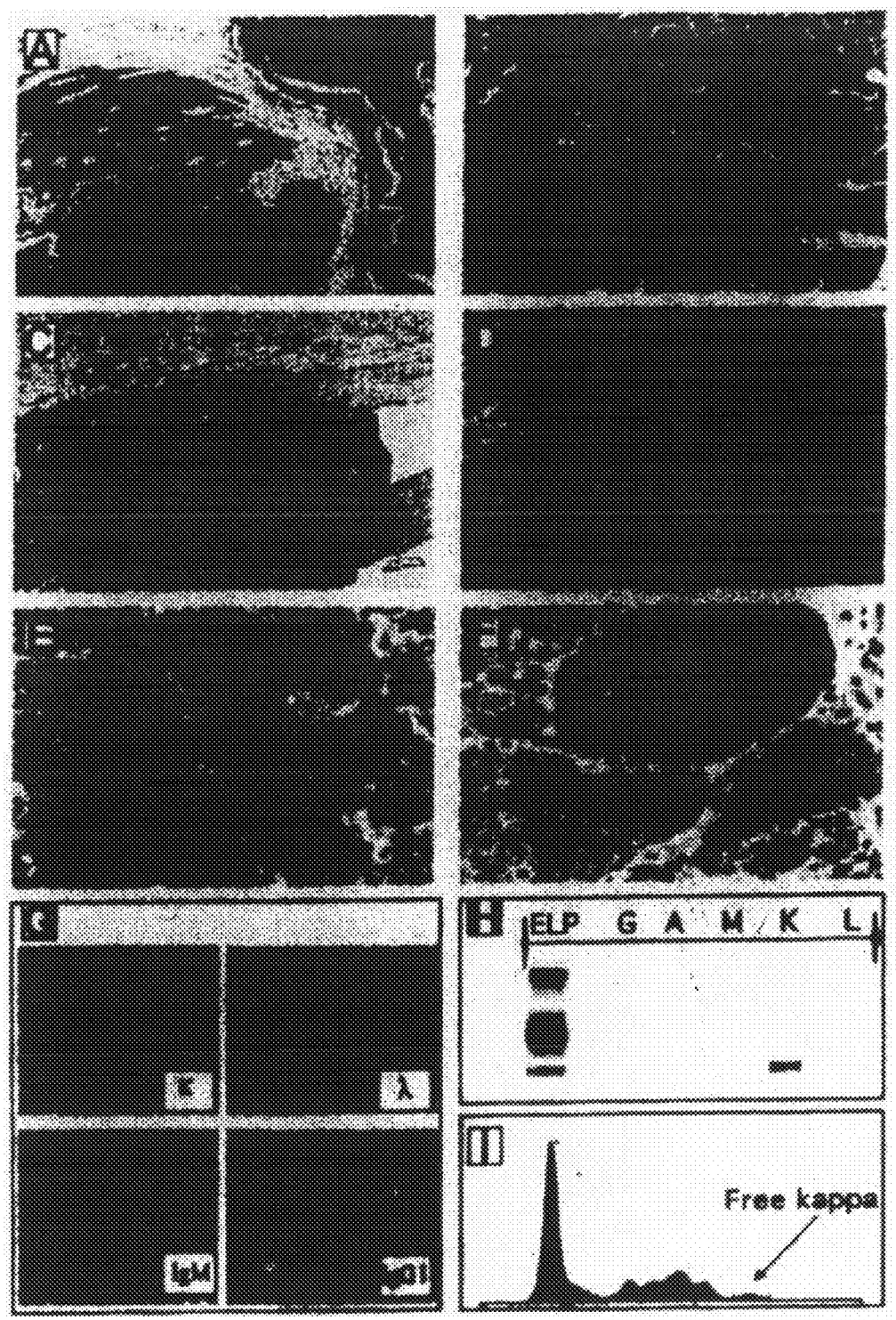
FIG. 6. Plasma cell immunophenotype and clonality. Plasma cell involving the bone marrow replaced the normal bone marrow and disrupted the bone trabeculae (A, 200×). Neoplastic plasma cells often infiltrated the perispinal tissues and ganglions (B, 200×) and in some cases invaded the central nervous system (C, 200×). NPM-ALK was largely confined within the cytoplasm of the neoplastic plasma cells (D, 400×). Tumor cells were invariably CD138+ (E, 400), displayed a variable number of Ki-67+ cells (F, 400×) and they expressed clonotype heavy and light immunoglobulin determinants (G, 100×). The serum analysis also demonstrated the presence of free light chain immunoglobulin (H-I).

Mice from N1, N14 and N16 lines were healthy up to 5-7 weeks of life. After the 5th week, Tg animals started to develop tumors. Survival curves obtained from 86 mice for the N16 line and 110 mice for the N1 line showed a mean survival of 18.5 (FIG. 4a), and 17 weeks (FIG. 4b), respectively, with a overall incidence of 100% for both lines. Tumors were mainly represented by thymic lymphomas or plasma cell neoplasms (FIG. 5 and FIG. 6) and all three lines developed, albeit with different frequencies, both thymic lymphomas and/or plasma cell tumors. Mice belonging to the N1 line showed, in fact, a prevalence of plasma cell tumors (>80%), in contrast to N16 mice which more often developed thymic lymphomas (>90%). Thymic and plasma cell tumors occurred with a similar frequency (50%) in mice of the N14 line. In rare cases (less than 5% overall), neoplasms characterized by atypical, spindle cells within a dense connective tissue were found. In addition, rare tumors (<1%) characterized by immature cells with abundant cytoplasm lacking either T or B cell markers, but expressing CD11b were identified. These tumors involved central and peripheral lymphoid tissues and were often observed infiltrating the liver, kidneys, lungs and other internal organs.

Figure 4:
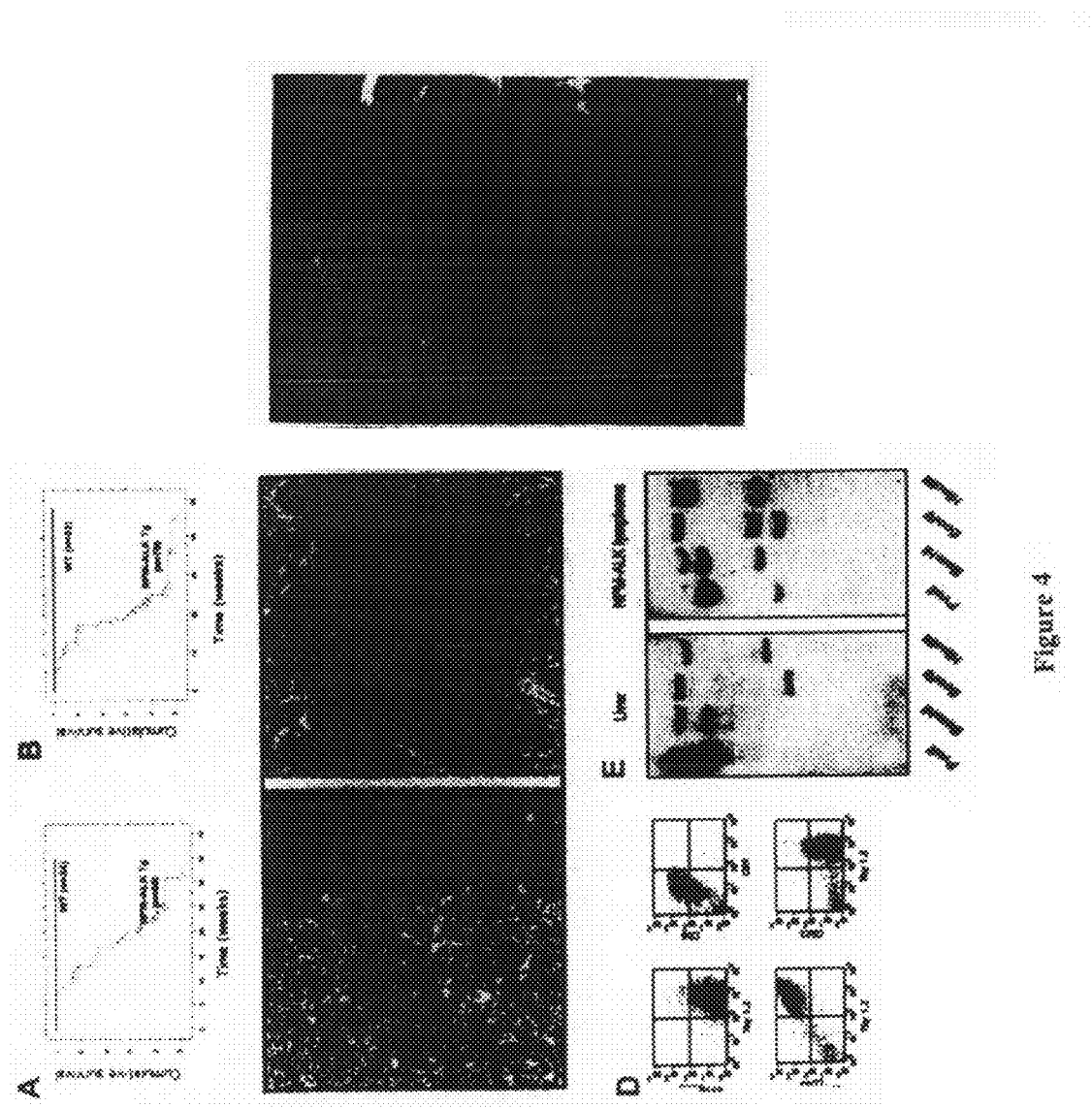
FIG. 4. NPM-ALK Tg mice develop lymphomas. Survival curves NPM-ALK Tg lines N16 (A) and N1(B). (C) Thymic lymphomas. Thymic lymphomas were composed of a homogeneous population of medium-sized lymphoid cells. Numerous mitosis and apoptotic bodies were present (left panel, 100×) (Ki67 positive cells were documented by immunohistochemistry, insert; 200×). Immunohistochemical staining with anti-ALK Ab demonstrated a nuclear and cytoplasmic expression of the NPM-ALK fusion protein (right panel, 100×). (D) Typical phenotype of thymic lymphomas. Tumor cells obtained from neoplastic thymus were stained with the indicated Abs and analyzed (Thy1+, B220−, CD44+, CD8+, CD4+/−, CD25−). (E) Southern blot analysis of NPM-ALK lymphomas showing a rearranged pattern of the T-cell receptor with all the enzymes used for digestion. Germline liver DNA was used as control. (F) NPM-ALK T-cell lines established tumors in immunodeficient mice. Tumor cells ($2\times10^6$) (NPM-ALK-Ova) were injected subcutis, and animals were followed daily for 4 weeks (upper panel). Tumors were composed of medium-sized blasts (lower panel, 400×) with high proliferation index (anti-Ki67 staining in the insert, 200×).

The mediastinal T cell lymphomas were composed of medium-sized lymphoblasts, with a relatively high mitotic index (10-15 mitosis/10 hpf) and high proliferation index as demonstrated by anti-Ki-67 staining (FIG. 4d). These immature thymocytes were always Thy-1+ and CD44+ but B220−. The expression of other antigens was variable. The majority of the tumors lacked CD4, CD8, CD3 and TCR but a fraction was CD4±/CD8+, CD3+/−, and CD30+ (FIG. 4c). Their clonal nature was documented by Southern Blot analysis (FIG. 4e). Moreover, in a limited number of cases, classical cytogenetic analysis, which documented a normal karyotype (date not shown) was performed. Finally from a representative group of these tumors, nine different cell lines, whose immunophenotypes matched those of the corresponding primary tumors were established. All these tumor cell lines grew efficiently in soft agar and in immunodeficient mice (Rag2−/−) after subcutaneous or intravenous injections (FIG. 4f).

Plasma cell tumors could be categorized into three major groups based on their cytological features. The first group included tumors composed primarily of mature plasma cells characterized by a large cytoplasm, eccentric and sometime binucleated nuclei with evident nucleoli. The second group included tumors with large, atypical cells with irregular nuclei and conscious nucleoli. Finally, a subset of these neoplasms displayed very atypical, pleomorphic/anaplastic cells (FIG. 5a-d). Plasmacytomas occurring in lymph nodes, spleen, and very rarely the thymus, often completely replaced these lymphoid organs and invariably invaded the surrounding tissues. Furthermore, in a substantial subset of the transgenic mice (20%), the neoplastic plasma cells occupied the bone marrow spaces and invaded into the vertebral bones, compressing and often destroying spinal ganglia and nerves (FIG. 6a, b). In rare instances the neoplastic cells, growing within the peri-spinal spaces, even reached the central nervous system (FIG. 6c). These histological findings corroborated the frequent gross limb paralysis of these mice and other postural and behavioral (spinning and rotational) habits. Notably, these plasma cell tumors occurred with the same frequency in mice crossed in C57BL/6 and Balb/c backgrounds. Immunophenotypic analysis of these neoplasms demonstrated that these tumors rarely expressed B220/CD45R but were invariably NPM-ALK (FIG. 6d) and CD138 positive (FIG. 6e). The proliferation rate as measured by the Ki-67 staining was variable ranging from 10% to 40% (FIG. 6f). The B cell origin of these tumors was further confirmed by the Southern Blotting (FIG. 7a) and by ELISA (data not shown). Furthermore, immunohistochemical staining performed on paraffin embedded tissue samples demonstrated the clonotypic expression of heavy and light chain of these tumors (FIG. 6g). Moreover, free light chain immunoglobulin were demonstrated in animals carrying plasma cell neoplasms (FIG. 6l, m). Collectively, these findings demonstrate that these neoplasms express clonal immunoglobulin, which can be secreted and detected in the serum.

Figure 7:
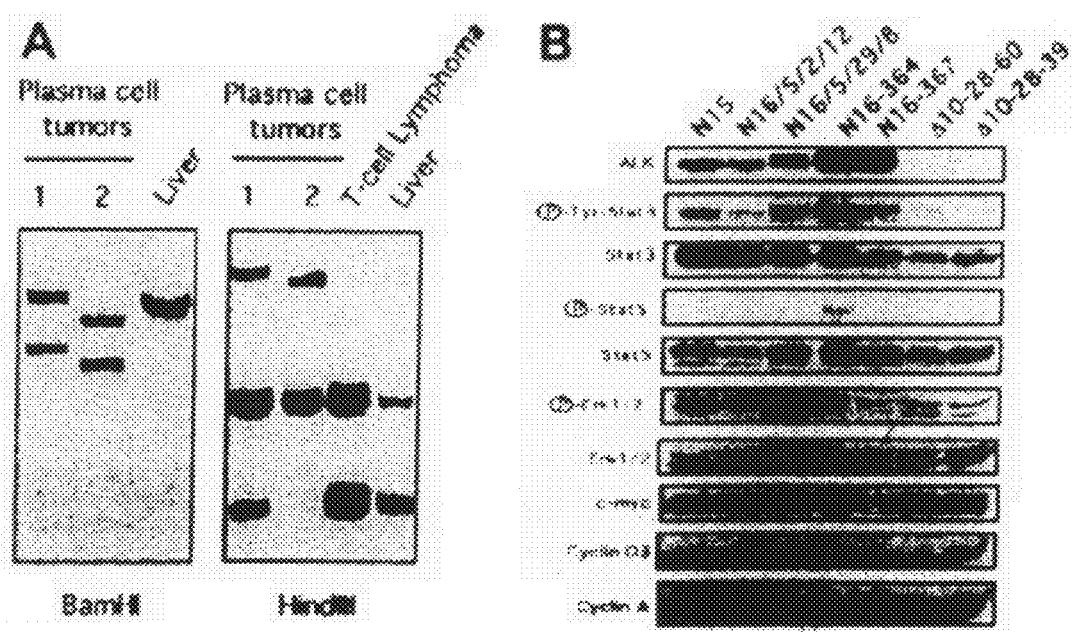
FIG. 7. Plasma cell and NPM-ALK tumors. (A) Southern blot analysis of plasma cell tumors showing rearranged pattern of the immunoglobulin gene. Germline liver DNA was used as control. (B) Constitutive expression of Stat3 in NPM-ALK tumor cells. Total cell extracts from NPM-ALK+ cell lines (lanes 1,2) and from fresh tumors were immunoblotted with the indicated antibodies. Thymic tumor derived from Δcul1 transgenic mice served as controls.

Finally, the expression profiles of several cell cycle regulators and Stat3 and Stat5 in fresh tumor samples and in three NPM-ALK T cell lines was investigated. All NPM-ALK positive samples showed the constitutive expression of phosphorylated Stat3 (FIG. 7b). On the other hand, on a single NPM-ALK case displayed very low levels of phosphorylated Stat5, despite the relatively high levels of Stat5. Interestingly the expressions of c-myc, phospho-Erk-1/2, and cyclin A and D3 were similar in NPM-ALK and in Δcul1 tumors (FIG. 7b). Δcul1 tumors were used as control because these tumors show a phenotype similar to that observed in NPM-ALK mice and because the Δcul1 expression was achieved using the same transgenic cassette. Overall, these findings confirm that NPM-ALK Tg neoplastic T cells express high levels of phosphorylated Stat3 and parallel the findings in human ALCL (Zhang, Q. et al. (2002) J Immunol. 168:466-474 and Zamo, A. et al. (2002) Oncogene. 21:1038-1047).

The results shown herein demonstrate a new mouse model of NPM-ALK-induced lymphomagenesis and have demonstrated that human NPM-ALK leads invariably to the generation of T cell lymphomas and plasma cell tumors. Our findings show that ALK can efficiently bind a series of mouse adaptor proteins and result in the constitutive activation of Jak3 and Stat3. The in vivo studies demonstrated that the constitutive activation of ALK can successfully prompt, with a relatively short latency, spontaneous lymphomagenesis in all mice. The efficient ability of activated ALK to induce transformation may be due to the diversity and complexity of the ALK signaling pathway. In fact, we have shown that PI3K, PLC-γ, Ras and Jak3-Stat3 pathways can be simultaneously activated Together with T-cell lymphomas, NPM-ALK Tg mice also developed ALK positive plasma cell tumors. The B cell origin of these tumors was confirmed by the presence of specific heavy chain immunoglobulin gene rearrangements and by expression of B-cell/plasma cell associated antigens CD45R and CD138. NPM-ALK Tg mice are a suitable model to study plasma cell tumors and, in particular, multiple myeloma. In fact, in addition to peripheral plasma cell tumors, 20% of the Tg mice displayed primary neoplasms within the bone marrow often involving the dorsal vertebrae. These tumors led to the compression and/or infiltration of ganglia and spinal nerves and ultimately resulted in the paralysis of the posterior legs. The clinical presentation and histologic features of these tumors closely recapitulated those of human multiple myelomas. Therefore NPM-ALK transgenic mice represent the only murine model for multiple myeloma. In conclusion, the findings have confirmed the tumorigenic activity of ALK in vivo and shown that ALK can efficiently transform T lymphocytes and lead to the development of plasma cell neoplasms. This model will provide a valuable tool to dissect the signaling of ALK and to identify new putative recurrent aberrations cooperating with ALK in promoting T cell transformation. The NPM-ALK mice are the first in vivo murine model for multiple myeloma and represent a unique model in which to investigate the efficacy of new therapeutic approaches for the treatment of both ALCL and multiple myelomas.

Example 2

Stable Small Interfering RNA Against Oncogenic ALK Induces Cell Death of Human Anaplastic Large Cell Lymphoma (ALCL) Cells shRNA Sequences and Plasmids Several short hairpin (sh) oligonucleotides (Invitrogen, Carlsbad, Calif., USA) directed against different regions of the cytoplasmic domain of the ALK tyrosine kinase were synthesized. The sense strands of the shRNA inserts were as follows:

```
ALK1(A1):
gatccccGTGGCTGTGAAGACGCTGCttcaagagaGCAGCGTCTTCACAG-

CCACttttttggaaa;
(SEQ ID NO: 1)

ALK2(A2):
gatccccTACTATAGAAAGGGAGGCTttcaagagaAGCCTCCCTTTCTAT-

AGTAttttttggaaa;
(SEQ ID NO: 2)

ALK3(A3):
gatccccTTACGGCTACCAGCAACAGttcaagagaCTGTTGCTGGTAGCC-

GTAAttttttggaaa;
(SEQ ID NO: 3)

ALK4(A4):
gatccccGCCCTGATCATCAGCAAATttcaagagaATTTGCTGATGATCA-

GGGCttttttggaaa;
(SEQ ID NO: 4)

ALK5(A5):
gatccccGGGCGAGCTACTATAGAAAttcaagagaTTTCTATAGTAGCTC-

GCCCttttttggaaa;
(SEQ ID NO: 5)

ALK 6(A6):
gatccccGCAAGAATAGCATGAACCAttcaagagaTGGTTCATGCTATTC-

TTGCttttttggaaa.
(SEQ ID NO: 6)
```

The 19 nt ALK target sequences are indicated in capital letters, meanwhile the hair pin and the sequences necessary for the directional cloning into the corresponding cassettes are depicted in small letter. Restriction endonuclease (5-BlgII and 3-HindIII) sequences for the directional cloning into pSuper and pSuperior pSuperior-EGFP-Retro vectors (Oligoengine, Seattle, Wash., USA) were included in each oligonucleotide. Oligonucleotides were purchased by InVitrogen (InVitrogen, Inc,). Single stands ALK oligonucleotides were first annealed and cloned into the BglII-HindIII sites of expression vectors as described (Brummelkamp. T R, Bernards R, Agami R. (2002) A system for stable expression of short interfering RNAs in mammalian cells. Science. 296 (5567):550-3). The fidelity of cloned double stranded DNA was confirmed by DNA sequencing of both DNA strands using specific oligoprimers, designed following the manufactures' recommendations.

Cassettes containing the Hi promoter and shALK sequences were subcloned into a pSuperRetro vector (Oligoengine) previously modified by the insertion of a CMV-EGFP (XhoI-blunt) reporter to yield the pSuperRetro-GFP (pSRG-ALK).

Lentivirus Cassettes.

NPM-ALK or ATIC-ALK or ALK-R expression was achieved using Pallino [Zamo, 2002 #101], an episomal retroviral expression vector carrying EGFP under the transcriptional activity of the Moloney Leukemia terminal repeat region (LTR-5').

The inducible expression of NPM-LAK was obtained using a Tet-Off bidirectional pBI-EGFP vector (Clontech) in which the NPM-ALK was sub-cloned after blunting (Hind III-Xho I) into Mlu I cloning site. NPM-ALK expression was repressed by culturing NPM-ALK+MEF-3T3 Tet-Off cells (Clontech, Palo Alto, Calif., USA; from now on for brevity MEF Tet-Off) in the presence of doxycyclin (10 µg/ml).

Cell Culture, Transfection and Retroviral Infection

Transfections of HEK-293T, GP-293, and MEF Tet-Off cells were performed with Effectene reagent (Qiagen, Valencia, Calif., USA), according to the manufacturer's instructions.

The NPM-ALK MEF Tet-Off cell line was generated by co-transfecting pBI-EGFP-NPM-ALK and a puromycin-resistance carrying vector in MEF Tet-Off cells. Multiple puromycin-resistant clones were selected based on their lowest basal NPM-ALK protein expression in absence of tetracycline and their highest expression in absence of the inducible drug.

Retroviral supernatants were produced by co-transfection of GP-293 packaging cells with pSRGA$_x$ and pVSV-G (Clontech, Palo Alto, Calif., USA); virus-containing supernatants were collected at 48, 72 and 90 hours, filtrated and concentrated by centrifugation. Aliquots of virus, plus 4 mg/ml of polybrene, were used to infect exponentially growing MEF or lymphoma cells ($1 \times 10^5$/ml). Fresh medium was supplemented at 24 hours after the infection (1:1). Infected NPM-ALK MEF Tet-Off cells with pSRG retroviruses were enriched by selection with puromycin (1 mg/ml, for 7 days). Transfection and infection efficiencies were calculated using the percentage of GFP positive cells, identified using fluorescence microscopy (Leica IM RE2) or flow cytometry (FACSCalibur, BD Biosciences, San Josè, Calif., USA).

HEK-293T (ATCC), GP-293 (Clontech) packaging, and MEF Tet-Off cells, were cultured under standard conditions (37° C. in humidified atmosphere, with 5% CO$_2$) in Dulbecco's modified Eagle's medium supplemented with 10% fetal calf serum (FCS). TS, Karpas 299 and SU-DHL (ALK+) and Jurkatt, CEM (ALK-) cells were grown in RPMI 1640 medium with 10% FCS.

Western Blotting

For Western Blot analysis, cells were lysed (50 mM Tris-HCl, pH 7.4, 150 mM NaCl, 0.1% Triton X-100, 5 mM EDTA, 1 mM $Na_3VO_4$, and 1 mM phenylmethyl sulfonyl fluoride and protease inhibitors). Total protein lysates (20 μg) were electrophoresed in SDS-PAGE gel and transferred onto nitrocellulose membranes. The filters were first blocked (5% low fat milk in PBS with 0.1% Tween 20; 1 h at RT), and then incubated with the primary antibodies for 1 hour at room temperature. After three washes, filters were incubated with horseradish peroxidase-conjugated goat anti-mouse or anti-rabbit antibodies (1:5000; Amersham) for 1 hour at room temperature. Detection of immunocomplexes was performed with an enhanced chemiluminescence system (ECL, Amersham, Piscataway, N.J., USA).

The following primary antibodies were used: mouse anti-ALK (clone; Zymed, South San Francisco, Calif., USA); mouse anti-α-tubulin (clone; Sigma Aldrich, St. Louis, Mo., USA); mouse anti-p27 (cloneTransduction Laboratories, KY, USA); mouse anti-PCNA (DAKO, Fremont, Calif., USA); mouse anti-JunB and mouse anti-cyclin D (clones; Santa Cruz Biotechnology, Santa Cruz, Calif., USA); rabbit anti-phosphoSTAT3, Tyr705 (CellSignaling, Beverly, Mass., USA); rabbit anti-cyclinE (M20, Santa Cruz Biotechnology, Santa Cruz, Calif., USA).

Tumor Growth in Nude Mice

NPM-ALK MEF Tet-Off cells were infected with pSRG or pSRG-A5 supernatants and puromycin-selected in presence of doxycyclin; NPM-ALK expression was achieved by the removal of doxycyclin and confirmed by Western blotting. Highly enriched GFP+ cells (>90%) cells ($1\times10^6$) were injected subcutaneously in athymic Nu/Nu mice, after 48 hours post-doxycyclin release. Tumor growth volumes were scored weekly, over a period of 4 weeks.

Cell Cycle and BRDU Cell Growth Analyses

Confluent monolayers of puromycin selected NPM-ALK MEF Tet-Off cells transduced with pSRG or pSRG-A5 were synchronized in G0/G1 by 0.2% serum after starvation for 72 hours. Cells were then harvested for cell cycle analysis and Western blotting. For DNA content analysis, cells were fixed for 1 hour in 70% ethanol at 4° C. After washing, cells were treated with RNase (0.25 mg/ml) and stained with propidium iodide (50 mg/ml). The $G_1/G_0$-phase fraction was calculated using the CellQuest program (Becton-Dickinson).

BRDU Determination

For BRDU determination $2\times10^6$ cells were cultured ($1\times10^6$/ml) with 10 μM BRDU for 2 hours at 37 C. Cells were then fixed and permeabilized using the Cytofix/Cytoperm reagents and the cells were then DNase digested according to the protocol provided by the manufacturer (BD Pharmingen). BRDU incorporation was detected by incubating target cells with 5 μl of anti-BRDU-APC in 100 μl of staining buffer. Cells were incubated (20 min at RT in the dark) and subsequently washed and analyzed using a FACSCaliber and CellQuest Pro software (BecktonDickinson). Cell proliferation and viability were also determined by a vital-dye exclusion assay (Trypan blue, 0.1%).

Mitochondrial Cell Staining

One million cells were incubated with 200 nM Mitotracker Red for 15 minutes at 37 C in media according to the manufacturer's instructions (Molecular Probes). Cells were then washed and analyzed using a FACSCaliber.

Results

Selection of anti-ALK shRNA.

ALK is the fusion partner of numerous oncogenic chromosomal translocations (Duyster J, Bai R Y, Morris S W. Translocations involving anaplastic lymphoma kinase (ALK).Oncogene. 10; 20(40):5623-37, 2001), thus targeting sequences shared by all ALK fusion chimeras by siRNAs could result in the inhibition of all ALK chimeric proteins and the ALK-R. Prospectively, this approach could be used against varioustumours carrying different fusion proteins or expressing deregulated ALK-R. Notably, the biological effects resulting from ablation of the ALK receptor in normal cells should be minimal in vivo, because ALK receptor expression is physiologically limited to neuronal cells, particularly during the embryonic life. Moreover, mice lacking ALK have no detectable phenotype.

Figure 8:
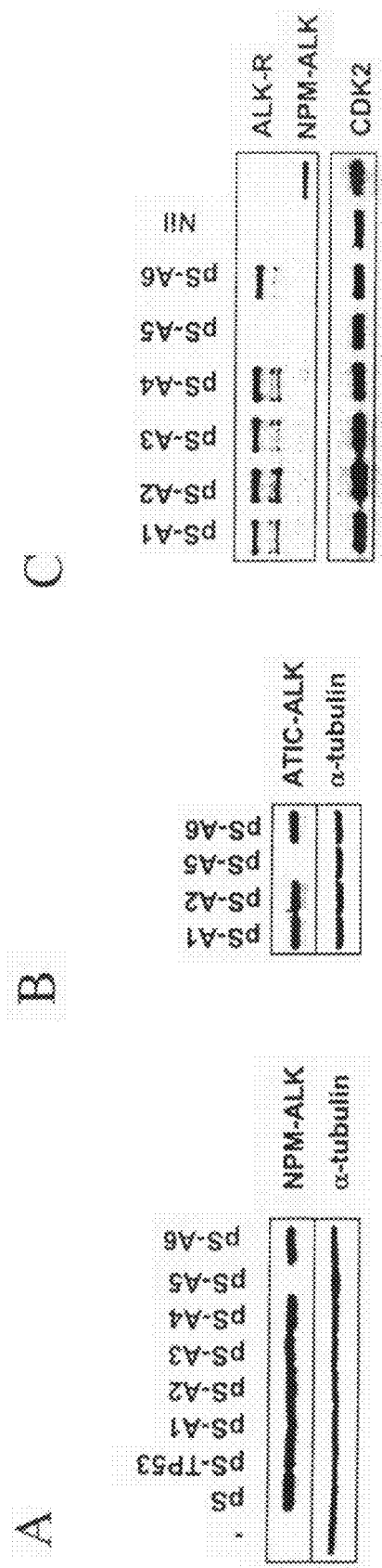
FIG. 8. Selection of anti-ALK shRNA. (A) ALK5 (A5) efficiently inhibits NPM-ALK protein expression. HEK-293T were co-transfected with Pallino NPM-ALK (2 μg) and one of six different pSUPER vectors carrying shRNA specific for ALK sequences (pS-A1-6)(8 μg). Cells were lysed 72 hours post-transfection and immunoblotted with the indicated antibodies. −=no transfection; A pSUPER-shRNA carrying a p53 specific sequence was used a unrelated control. (pS-p53) (B) ALK5 (A5) inhibits ATIC-ALK protein expression. HEK-293T were co-transfected with Pallino ATIC-ALK and pSUPER-ALK shRNA interfering sequences as above. Expression of ATIC-ALK protein was determined by Western blot analysis as described above. (C) ALK5 (A5) inhibits ALK receptor (ALK-R) protein expression. HEK-293T cells were co-transfected with Pallino ALK-R and pSUPER-ALK shRNA interfering sequences as above.

Six short interfering RNA sequences targeted against the cytoplasmic portion of ALK were generated. ALK siRNA vectors were first co-transfected with Pallino-NPM-ALK in HEK-293T cells. As shown in FIG. 8, only a single construct, designated as ALK5 (A5), efficiently down-regulated the protein level of NPM-ALK (>90%) after 48 hrs from transfection (FIG. 8A). An unrelated siRNA vector, known to inhibit the expression of p53 was used as a control showing that the expression of ALK was not changed after its transfection, despite the robust down-modulation of p53 (Data non shown) Similar findings were obtained using a pSUPER carrying TRP-MET sequences, supporting the specificity of our ALK siRNA construct. To further validate the efficacy of A5 against other ALK fusion proteins and the native ALK-R, we studied the expression of ATIC-ALK and ALK receptor in transfected HEK-293T cells and found that only A5 siRNA was able to successfully abrogate expression of both ALK proteins (FIGS. 8B and C). In sum, these findings demonstrate that the A5 can abrogate the expression of all ALK proteins and therefore could be used to specifically target the expression of these proteins in normal and neoplastic cells.

ALK siRNA Inhibits NPM-ALK-mediated Transformation of MEF Cells.

To investigate the biological changes resulting from the silencing of ALK fusion proteins the transformation efficacy of NPM-ALK in the presence of ALK-5 siRNA was studied. To accomplish this goal an inducible system in which ALK-mediated transformation is tightly regulated after doxycyclin withdrawal was used. MEF carrying the NPM-ALK Tet-Off cassette were infected with ALK-5 pSuperRetro virus in presence of doxycyclin. The percentage of infected cells prior to and following puromycin selection was monitored using GFP expression. FIG. 9A shows a significant down-regulation of NPM-ALK protein expression after doxycyclin withdrawal in the presence of ALK-5 siRNA, which is proportional to the percentage of GFP positive cells.

Since NPM-ALK leads to STAT3 phosphorylation and results in a strong trans-activation of Jun-B (Chiarle, in preparation), we tested whether these downstream signalling molecules were down modulated in the presence of ALK-5 siRNA. It was determined that the levels of phosphorylated Stat3 and total JunB were significantly diminished in cells transduced with the ALK-5 pSuperRetro construct (FIG. 9A).

Serum-deprived MEF cells expressing NPM-ALK acquired the capability to escape $G_0/G_1$ arrest, however, when infected with the pSRG-A5 retrovirus they revert and display a partial restoration of the $G_0/G_1$ arrest (FIG. 9B). Moreover, these changes were associated with markedly lower levels of cyclin D1 and cyclin E expression and decreased PCNA expression (FIG. 9C).

Figure 9:
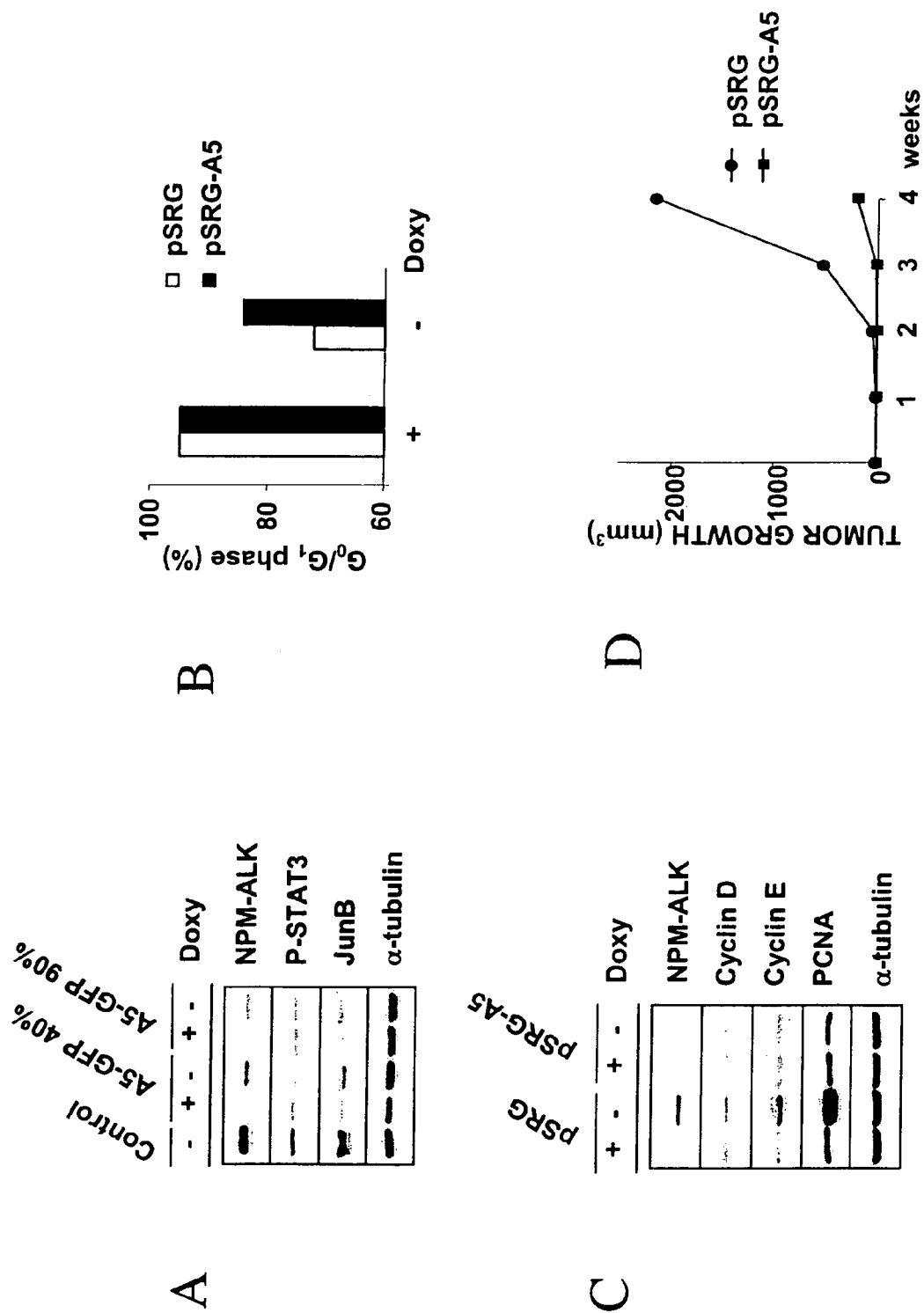
FIG. 9. Anti-ALK siRNA inhibits NPM-ALK-mediated transformation of MEF cells. (A) Suppression of NPM-ALK expression leads to down-regulation of known downstream targets of ALK. MEF NPM-ALK Tet-Off cells were infected with pSRG-A5 virus, transduction efficiency was assessed 72 hours post-infection by FACS analysis of GFP (40%). pSRG-A5-infected cells were further enriched by selection with 1 mg/ml puromycin for 1 week (90%). NPM-ALK expression was inhibited by doxycyclin withdrawn. Protein expression was evaluated culturing (72 hr) semi-confluent cells in absence of doxycyclin. (B) shRNA A-5 expression leads to G0/G1 cell cycle arrest. DNA content analysis was performed in cells grown to confluence and kept in 0.2% serum medium for 72 hours in presence of absence of doxycyclin. Cells were then listed and analysed by Western blotting with indicated antibodies. (D) pSRG-A5 expression prevents MEF NPM-ALK cell growth in deficient mice. MEF NPM-ALK Tet-Off cells were first infected and then selected in puromycin and highly enriched GFP+(>90%) MEF (106 cells/mouse) were inoculated subcutaneously into nude mice recipients. Tumor growth was monitored weekly for 4 weeks.

Since NPM-ALK expression in MEF cells leads to relevant morphological changes including cell elongation, bipolarized formations and loose plate attachment, the effect of inhibition of NPM-ALK expression on the phenotype of these cells was then studied. Notably, MEF-NPM-ALK cells, after infection with A5 shRNA construct, expressed very low levels of NPM-ALK and regained their normal pre-transformed cellular features. Furthermore, highly enriched GFP+, puromycin resistant pSRG-A5MEF-NPM-ALK cells injected into athymic Nu/Nu mice ($1\times10^6$ cells) grew poorly compared to control infected cells (FIG. 9 D).

ALK-RNAi Inhibits Cell Growth and Induces Cell Death in Human ALCL Cells, in vitro.

Figure 10:
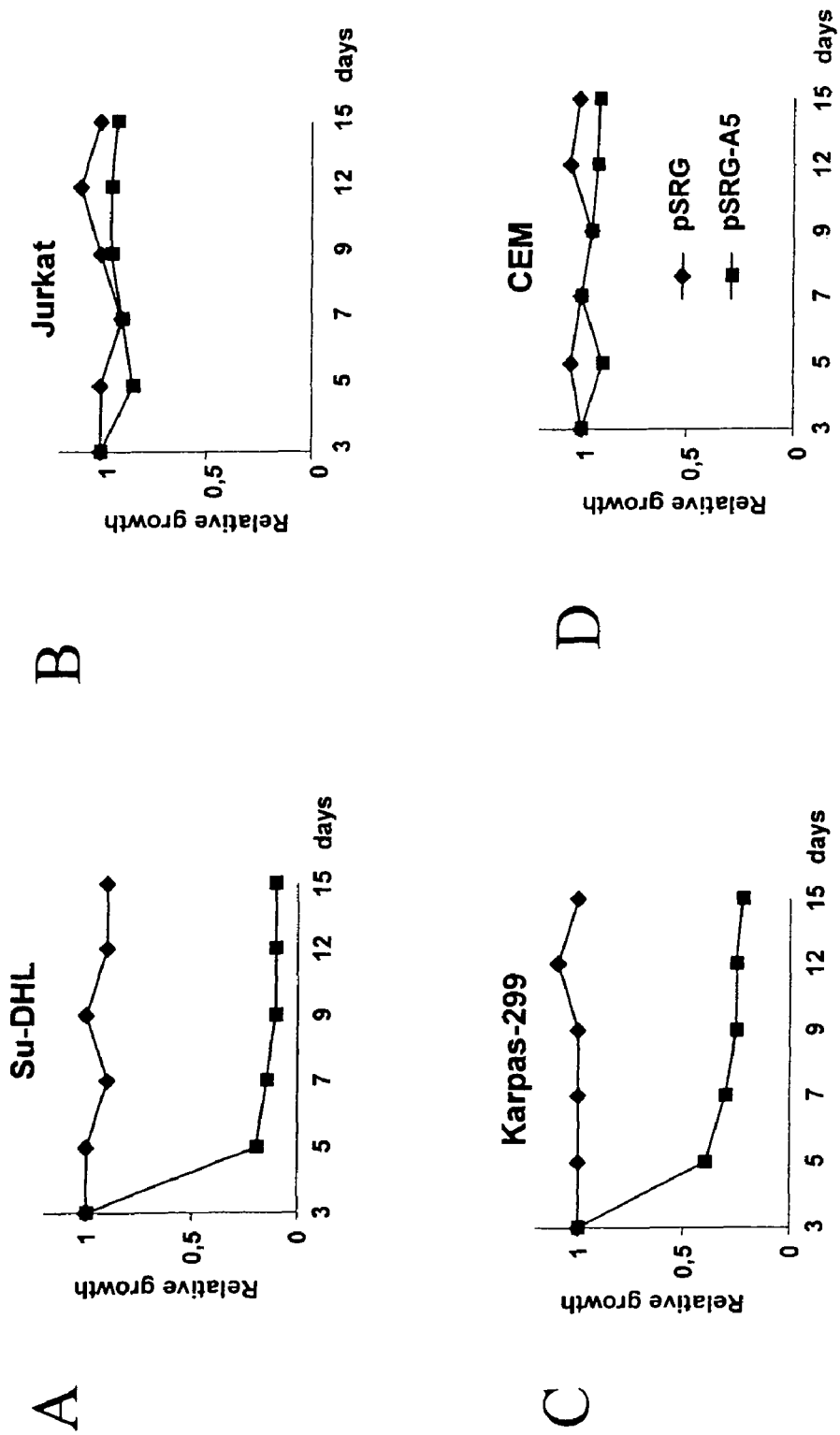
FIG. 10. Anti-ALK siRNA inhibits the growth of human ALCL cells. ALK+(SU-DHL-1 [A], Karpas 299 [C], ALK−(Jurkat [B] and CEM [D]) lymphoblastoid cell lines were transduced, with either GFP empty (pSRG) or the pSRG-A5 vectors. The percentage of GFP-positive cells was determined by flow cytometry and monitored every 48 hours beginning at day 3 post-infection for a period of 15 days.

The effect of the siRNA construct A5 was subsequently tested in multiple human ALK-positive ALCL cell lines. Jurkat and CEM were used as ALK-negative lymphoblastoid controls. To determine if interfering with NPM-ALK expression would lead to a specific inhibition of ALK-positive cell growth, lymphoid cells were transduced with pSRG-A5, pSRG-A6 and pSRG vectors. The percentage of the GFP-positive cells was evaluated over time. In each experiment, the initial percentage of GFP-positive cells, determined by FACS analysis 3 days after infection, ranged from 15% to 70%, with TS being the most efficiently transduced. The percentage of GFP-A5 positive cells decreased overtime in all ALK+ cell lines (FIG. 10 A and C), contrary to percentage of GFP+A5 CEM and Jurkat cell lines, which remained stable (FIGS. 10B and D)). No changes were observed in control pSRG-A6 and pSRG-GFP+ALK+ cells. Similar findings were obtained with murine NPM-ALK positive neoplastic T-cells derived from T cell lymphoblastic lymphomas of NPM-ALK Tg mice. Overall, these findings suggest that the down-regulation of ALK result in significant growth impairment.

To determine the putative changes in protein levels of endogenous NPM-ALK in ALCL cells transduced with A-5 shRNA retroviruses, transduced cells were enriched by FACS sorting and ALK expression levels were determined by western blotting. pSRG transduced cells were used a control. As shown in FIG. 10G, a small but reproducible loss of ALK was observed.

To clarify whether the growth disadvantage induced by NPM-ALK knockdown in ALCL cells was a consequence of reduced proliferation and/or increased propensity to undergo cell death, TS cells were infected with A5-pSGFP retroviral vector and the percentage of S-G2 or BRDU positive cells was evaluated overtime among GFP− and GFP+ cells. Using this approach, it was demonstrated that the percentage of proliferating cells was substantially lower among ALK-5+ GFP+ cells than in GFP− cells within the same culture and among GFP+ cells transduced with control vectors.

Figure 11:
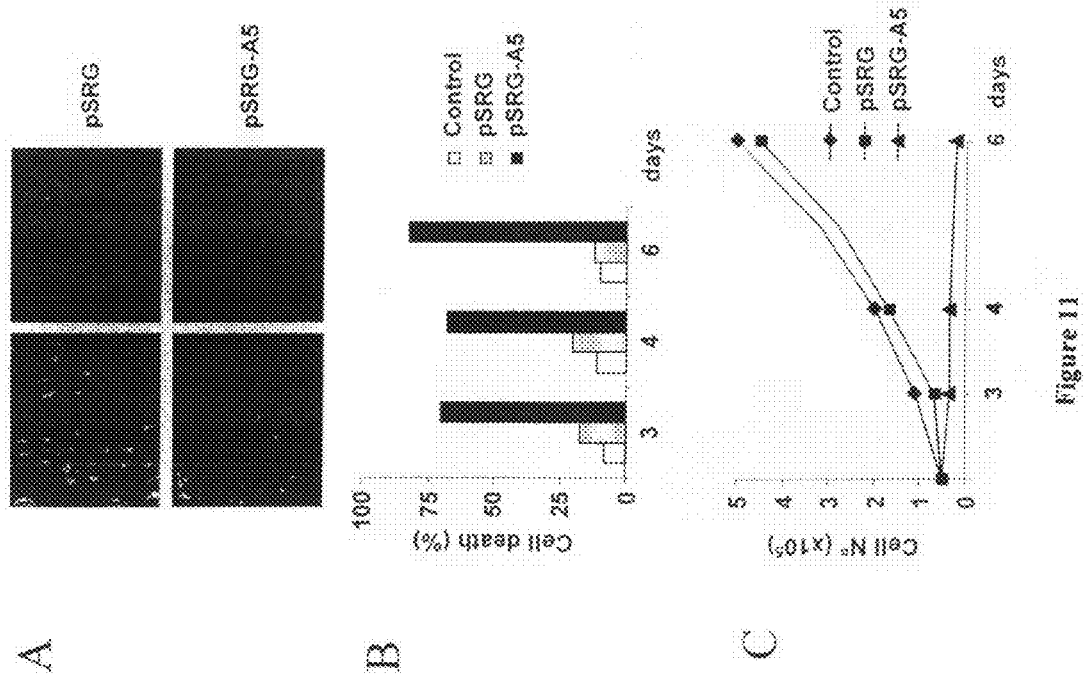
FIG. 11. Anti-ALK siRNA inhibits growth and induces cell death in TS cells. ShRNA A5 leads ALK+ ALCL cells to cell death. Human TS cells were transduced with pSRG or pSRG-A5 constructs, and after 2 post-infection, GFP-positive cells were sorted using MoFo sorter. (A) Highly enriched GFP+ cells (>95%) were evaluated (24 hours after sorting) using a light or fluorescent inverted microscope, (bright field: left panels). 5×103/well cells were plated (96-well plate) and the percentage of alive cells was calculated overtime (B). Total number of live cells was also calculated at day 3, 4 and 6 after sorting (C).

To study whether ALK siRNA could promote cell death, highly enriched A5-GFP-positive TS cells by cell sorting (>95% GFP) were evaluated by microscopy. As shown in FIG. 11A, after 24 hr from cell sorting all cells transduced with the control vector were viable and expressed detectable, although variable, levels of GFP. The majority (>50%) of ALK-5-transduced TS cells displayed shrunken, picnotic nuclei, became rifrangent and lacked detectable GFP expression. These findings were confirmed with enumeration of viable cells by trypan blue exclusion (FIG. 11B) and proliferating cell quantitation using total cell counts (FIG. 11C).

Figure 12:
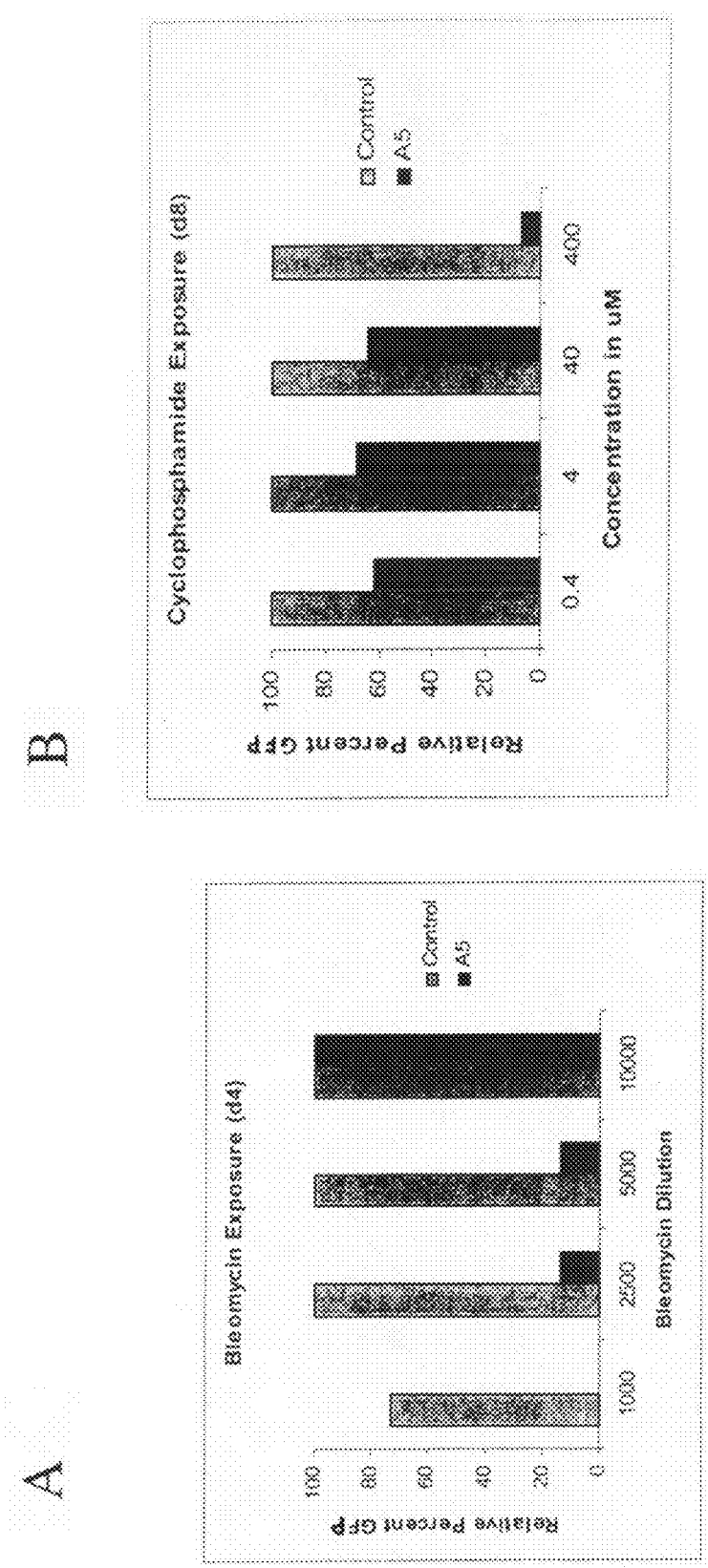
FIG. 12. Anti-ALK siRNA synergize with chemotherapeutic drugs. TS cells transduced with pSRG and pSRG-A5 were culture in presence of suboptimal concentration of drugs. Percentage of positive GFP positive cells was evaluated after 4 days (Bleomycin) and 8 days (cyclophosphamide).

Finally, it was demonstrated that decreased protein levels of ALK induced by shRNA A5-ALK retroviral viruses synergize with stress conditions to promote cell death. Toward this end, TS cells were infected with pSRG-A5 viruses and, after three days post-infection, were cultured in presence of sub optimal concentration of FCS. As shown in FIG. 11D, A5 transduced TS cells in the presence of 1% FCS decreased as percentage of total cells considerably faster than cells cultured in 10% FCS. In the same conditions, GFP negative cells survived and displayed higher proliferative rates (data not shown). Similar findings were observed when A5-GFP positive cells were grown in presence of sub-optimal concentrations of chemothepeutic agents (FIG. 12).

Figure 13:
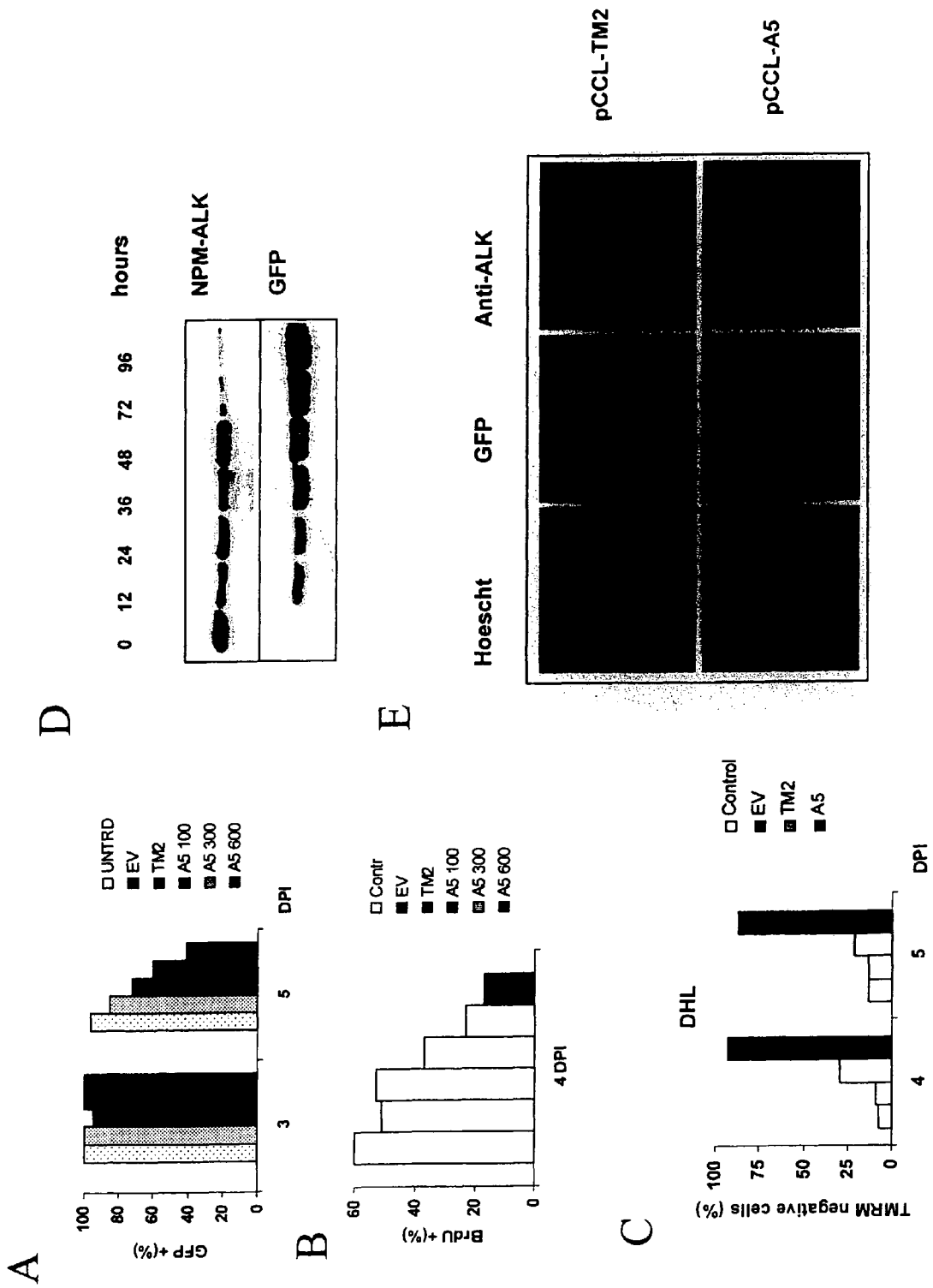
FIG. 13. Anti-ALK siRNA via lentivirus delivery efficiently inhibit NPM-ALK protein expression and leads to cell cycle arrest and cell death. Lentivirus transduction leads to high levels of infection. TS cells were infected lentivirus supernatant and the percentage of GFP positive cells was calculated at day 3 and 5 post infection (A). Anti ALK A5 leads to G0/G1 cell arrest. Cells infected with A5 undergo cell cycle arrest which directly proportional to lentivirus load (B) and to the loss of NPM-ALK protein expression (D and E). Percentage of TMRM positive cells was calculated after SU- DHL-1 transfection (day 4 post infection). Transfected cells (72 hr) with anti-ALK sh-RNA constructs were stained with anti-ALK antibody. Immunocomplexes were visualized using biotin-conjugated rabbit anti-mouse followed by Avidin-PE (E, right panel). Nuclei were identified using DAPI (left panels). GFP expression was also determined (central panels).
Figure 14:
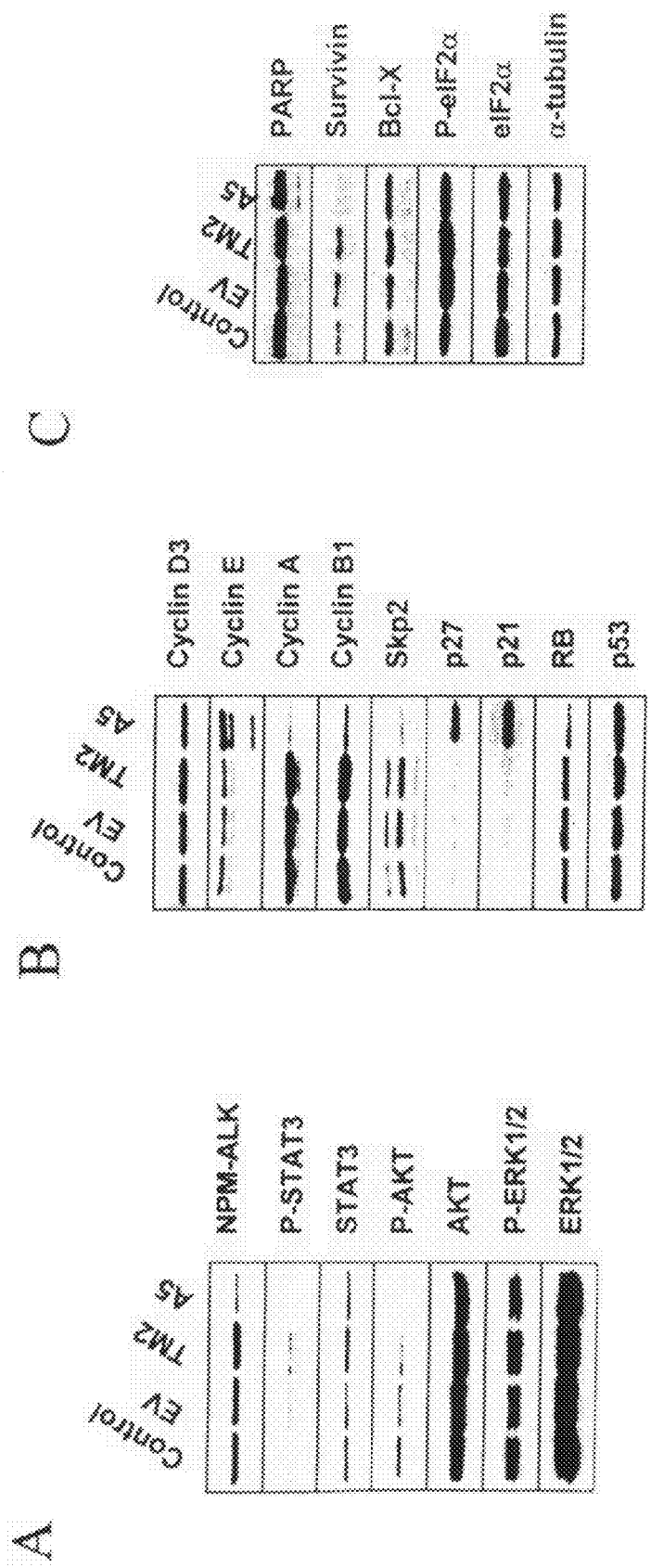
FIG. 14. Anti-ALK siRNA via lentivirus result in the inhibition of phosphorylation of known downstream ALK effectors and in the loss of Surviving protein expression. TS transfected cells (600) after 72 hr post infection were harvested and lysed. Protein expression was determined by Western blotting using specific antibodies as described.

In summary, these findings suggest that decreased levels of ALK compromise the growth of ALK+ positive cells and decrease reduce ability to growth and survive in stress conditions. The relatively long period of time required to achieve these effects might be due to the long half-life of NPM-ALK protein and the relatively low copy number of retroviruses found in human ALK positive cells. Since concentrated lentiviruses can more efficiently infect a higher percentage of cells and deliver greater numbers of transduced constructs, two lentivirus cassettes targeting ALK (A5) and a control gene MET (TM2) were generated. Even with very small amounts of virus, more than 95% of human ALK positive cells could be infected (FIG. 13A). Importantly, the relative intensity of GFP positive cells increased substantially when TS cells were transduced at higher concentrations (FIG. 13A), suggesting that in these conditions a larger amount of the desired constructs could be delivered and expressed into the target cells. As result, 5 days following infection, TS cells transduced with the highest viral load displayed a proportional G0/G1 block a lowest percentages of cells in S-phase (FIG. 13B) and lower percentages of GFP positive cells. Moreover these cells displayed the most significant loss of NPM-ALK expression (FIGS. 13D and E), the most decreased mitochrondrial function (FIG. 13C) and underwent Parp activation (FIG. 14). Overall, these findings indicate that highly concentrated lentivirus preparations of A5 substantially decreased the expression of NPM-ALK and lead to rapid cell cycle arrest, loss of mitochondrial redox and eventually cell death, as soon as 5 days post infection. These findings are consistent with those obtained using retroviral preparations. Finally, we also demonstrated that cells rendered unable to undergo cell death after retroviral infection underwent mitochondrial decay and apoptosis (data not shown) following transduction with concentrated A5-lentiviruses. These findings demonstrate that high level of siRNA must be delivered to achieve substantial abrogation of NPM-ALK expression and significant biological effects.

What is claimed is:

1. An isolated siRNA molecule, specific for the ALK tyrosine kinase gene, said siRNA encoded by SEQ ID NO:5, wherein said siRNA molecule inhibits the proliferation of tumor cells.

2. The isolated siRNA molecule of claim 1, wherein said inhibition of proliferation of tumor cells is the result of inhibition of expression of the ALK gene by said siRNA molecule.

3. A pharmaceutical composition comprising the isolated siRNA molecule of claim 1 and a pharmaceutically acceptable carrier, wherein said composition is effective in inhibiting the growth of tumor cells that contain the ALK gene.

* * * * *

SEQUENCE LISTING

<160> NUMBER OF SEQ ID NOS: 6

<210> SEQ ID NO 1
<211> LENGTH: 64
<212> TYPE: DNA
<213> ORGANISM: Artificial Sequence
<220> FEATURE:
<223> OTHER INFORMATION: synthetic

<400> SEQUENCE: 1
gatccccgtg gctgtgaaga cgctgcttca agagagcagc gtcttcacag ccactttttg    60
gaaa                                                                 64

<210> SEQ ID NO 2
<211> LENGTH: 64
<212> TYPE: DNA
<213> ORGANISM: Artificial Sequence
<220> FEATURE:
<223> OTHER INFORMATION: synthetic

<400> SEQUENCE: 2
gatcccctac tatagaaagg gaggctttca agagaagcct cctttctat agtattttg     60 gaaa                                                                 64

<210> SEQ ID NO 3
<211> LENGTH: 64
<212> TYPE: DNA
<213> ORGANISM: Artificial Sequence
<220> FEATURE:
<223> OTHER INFORMATION: synthetic

<400> SEQUENCE: 3
gatcccctta cggctaccag caacagttca agagactgtt gctggtagcc gtaattttg    60 gaaa                                                                 64

<210> SEQ ID NO 4
<211> LENGTH: 64
<212> TYPE: DNA
<213> ORGANISM: Artificial Sequence
<220> FEATURE:
<223> OTHER INFORMATION: synthetic

<400> SEQUENCE: 4 gatcccgcc ctgatcatca gcaaatttca agagaatttg ctgatgatca gggctttttg    60
gaaa                                                                 64

<210> SEQ ID NO 5
<211> LENGTH: 64
<212> TYPE: DNA
<213> ORGANISM: Artificial Sequence
<220> FEATURE:
<223> OTHER INFORMATION: synthetic

<400> SEQUENCE: 5 gatcccggg cgagctacta tagaaattca agagatttct atagtagctc gcccttttg    60 gaaa                                                                 64

<210> SEQ ID NO 6
<211> LENGTH: 64
<212> TYPE: DNA
<213> ORGANISM: Artificial Sequence

```
<220> FEATURE:
<223> OTHER INFORMATION: synthetic

<400> SEQUENCE: 6
gatccccgca agaatagcat gaaccattca agagatggtt catgctattc ttgctttttg      60
gaaa                                                                  64
```